US010112973B2

(12) United States Patent
Kretzschmar et al.

(10) Patent No.: US 10,112,973 B2
(45) Date of Patent: Oct. 30, 2018

(54) PROCESS FOR THE PREPARATION OF RAMIPRIL

(71) Applicant: SANOFI-AVENTIS DEUTSCHLAND GMBH, Frankfurt am Main (DE)

(72) Inventors: Gerhard Kretzschmar, Frankfurt am Main (DE); Jan Oehme, Frankfurt am Main (DE); Kai Rossen, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 15/317,362

(22) PCT Filed: Jun. 8, 2015

(86) PCT No.: PCT/EP2015/062632
§ 371 (c)(1),
(2) Date: Dec. 8, 2016

(87) PCT Pub. No.: WO2015/189108
PCT Pub. Date: Dec. 17, 2015

(65) Prior Publication Data
US 2017/0158733 A1 Jun. 8, 2017

(30) Foreign Application Priority Data

Jun. 11, 2014 (EP) ..................................... 14171915

(51) Int. Cl.
C07C 233/47 (2006.01)
C07K 5/062 (2006.01)
C07D 209/52 (2006.01)
C07C 249/02 (2006.01)
C07C 251/20 (2006.01)
C07C 255/46 (2006.01)

(52) U.S. Cl.
CPC ........ *C07K 5/06026* (2013.01); *C07C 233/47* (2013.01); *C07C 249/02* (2013.01); *C07C 251/20* (2013.01); *C07C 255/46* (2013.01); *C07D 209/52* (2013.01); *C07C 2101/08* (2013.01); *C07C 2101/10* (2013.01)

(58) Field of Classification Search
CPC .................................................. C07C 233/47
See application file for complete search history.

(56) References Cited

U.S. PATENT DOCUMENTS

| 5,055,591 | A | 10/1991 | Urbach et al. |
| 8,119,375 | B2 | 2/2012 | Berk et al. |
| 2007/0232680 | A1 | 10/2007 | Bolugoddu et al. |
| 2011/0257408 | A1 | 10/2011 | Liu et al. |

FOREIGN PATENT DOCUMENTS

| EP | 0079022 A2 | 5/1983 |
| WO | WO-85/04873 A1 | 11/1985 |
| WO | WO-2005/049567 A1 | 6/2005 |
| WO | WO-2005/049568 A1 | 6/2005 |
| WO | WO-2006/100168 A1 | 9/2006 |
| WO | WO-2009/098251 A1 | 8/2009 |
| WO | WO-2011/133651 A1 | 10/2011 |

OTHER PUBLICATIONS

Sarakinos, Georgios. Document No. 151:221459, retrieved from STN; Aug. 13, 2009.*
Avenoza, A. et al. (2007; e-published on Dec. 19, 2006). "Mechanistic Study of the Ring-Size Modulation in Michael-Dieckmann Type Reactions of 2-Acylaminoacrylates With Ketene Diethyl Acetal," *New Journal of Chemistry* 31:224-229.
Breuer, M. et al. (Feb. 6, 2004). "Industrial Methods for the Production of Optically Active Intermediates," *Angewandte Chemie International Edition* 43(7):788-824.
Cavé, C. et al. (Dec. 15, 1997). "Efficient Access to Virtually Enantiopure α-Dialkyl-, α-Acetoxy-, and α-Acetamido Esters," *Tetrahedron Letters* 38(50):8703-8706.
Drège, E. et al. (Nov. 19, 2010; e-published on Oct. 29, 2010). "A Facile and Stereocontrolled Synthesis of γ-Substituted γ-Fluoroglutamates by Conjugate Addition: Conflicting Effect between Fluorinated Enaminoester and Hinderered Michael Acceptor," *The Journal of Organic Chemistry* 75(22):7596-7604.
Eilingsfeld, H. et al. (1960). "Amidchloride and Carbamidchloride," *Angewandte Chemie* 72(22):836-845. Machine translation of the Abstract only.
Guingant, A. et al. (Jan. 1, 1991). "Synthesis of Optically Active α, α-Distributed β-Keto Esters via Chiral β-enamino Esters," *Tetrahedron: Asymmetry* 2(6):411-414.
Hendra, F. et al. (Mar. 22, 2004). "Asymmetric Michael Reaction Between a Chiral α,β-dimethyl-β-enamino Ester and α-substituted Acrylates," *Tetrahedron Asymmetry* 15(6):1027-1032.
Hughes, R.A. et al. (Nov. 9, 2005; e-published on Oct. 18, 2005). "Total Synthesis of the Thiopeptide Antibiotic Amythiamicin D," *J. Am. Chem. Soc.* 127(44):15644-15651.
Karl, U. et al. (Sep. Oct. 2009). "BASF's ChiPros® Chiral Building Blocks—The Corner Stones of your API Syntheses!," *Chimica Oggi* 27(5):66-69.
Kondaiah, G.C.M. et al. (2011; e-published on Mar. 21, 2011). "Asymmetric Synthesis of (S,S,S)-2-Aza-bicyclo-[3.3.0]-octane-3-carboxylic Acid Benzyl Ester: Formal Synthesis of Ramipril," *Synthetic Communications* 41(8).1186-1191.
Krawczyk, H. et al. (Mar. 20, 2006; e-published on Apr. 4, 2006). "Highly Enantioselective Synthesis of α-methylene-δ-valerolactones by an Asymmetric Michael Reaction," *Tetrahedron: Asymmetry* 17(6):908-915.
Leplae, P.R. et al. (2001). "An Efficient Route to Either Enantiomer of trans-2-Aminocyclopentanecarboxylic Acid," *The Journal of Organic Chemistry* 66(16):5629-5632.

(Continued)

*Primary Examiner* — Shawquia Jackson
(74) *Attorney, Agent, or Firm* — Morrison & Foerster LLP

(57) ABSTRACT

An enantioselective process for the production of (2S,3aS,6aS)-cyclopenta[b]pyrrole-2-carboxylic acid and its conversion into Ramipril is provided.

17 Claims, No Drawings

(56) References Cited

OTHER PUBLICATIONS

Liu, H. et al. (Feb. 17, 2003). "A Modified Robinson Annulation Process to α, α-disubstituted-β, γ-unsaturated Cyclohexanone System. Application to the Total Synthesis of Nanaimoal," *Tetrahedron* 59(8):1209-1226.
Malakondaiah, G.C. et al. (2008; e-published on May 9, 2008). "Expeditious Synthesis of Ramipril: An Angiotensin Converting Enzyme (ACE) Inhibitor," *Synthetic Communications* 38(11):1737-1744.
Navarre, L. et al. (2008; e-published on Apr. 9, 2008). "Access to Enantioenriched α-Amino Esters via Rhodium-Catalyzed 1,4-Addition/Enantioselective Protonation," *J. Am. Chem. Soc.* 130(19):6159-6169.
Panella, L. et al. (Mar. 3, 2006; e-published on Feb. 2, 2006). "Enantioselective Rh-Catalyzed Hydrogenation of N-Formyl Dehydroamino Esters With Monodentate Phosphoramidite Ligands," *J.Org.Chem.* 71(5):2026-2036.
Pizzonero, M. et al. (Nov. 28, 2005). "The Asymmetric Michael-type Alkylation of Chiral β-enamino Esters: Critical Role of a Benzyl Ester Group in the Racemization of Adducts," *Tetrahedron: Asymmetry* 16(23):3853-3857.
Torisawa, Y. et al. (Oct. 1992). "Diels-Alder Reactions of Dihydropyridinones: Synthetic Entry to the Manzamine A Tricyclic Core," *The Journal of Organic Chemistry* 57(21):5741-5747.
International Search Report dated Jul. 13, 2015 for International Application No. PCT/EP2015/062632 filed on Jun. 8, 2015, four pages.
Written Opinion of the International Searching Authority dated Jul. 13, 2015 for International Application No. PCT/EP2015/062632 filed on Jun. 8, 2015, six pages.

\* cited by examiner

PROCESS FOR THE PREPARATION OF RAMIPRIL

CROSS REFERENCE TO RELATED APPLICATIONS

This application is a National Phase application under 35 U.S.C. § 371 of International Application No. PCT/EP2015/062632 filed Jun. 8, 2015, which claims priority benefit to EP Application No. 14171915.3 filed Jun. 11, 2014, the disclosures of each of which are herein incorporated by reference in their entirety.

The present invention relates to a new process for making Ramipril. The present invention further relates to an improved process for preparing (2S,3aS,6aS)-cyclopenta[b]pyrrole-2-carboxylic acid as an intermediate for manufacturing Ramipril. The present invention also relates to new intermediates and to a process for making them.

Ramipril as shown in formula (I) is a known ACE inhibitor which is frequently employed in pharmacy to treat high blood pressure (hypertension), heart failure and related diseases.

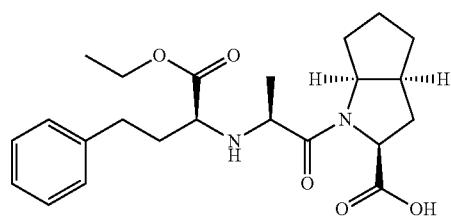

The production of Ramipril involves the coupling of the amino acid N-[1-(S)-(ethoxycarbonyl)-3-phenylpropyl]-L-alanine as shown in formula (II) and of the amino acid (2S,3aS,6aS)-cyclopenta[b]pyrrole-2-carboxylic acid as shown in formula IIIa (R=H). Alternatively, Ramipril is produced by coupling of compound (II) and the benzyl ester derivative IIIb (R=Bn) and subsequent debenzylation by hydrogenolysis.

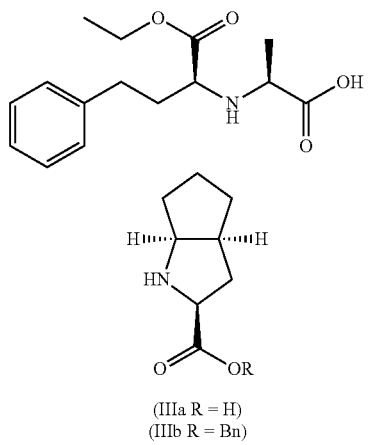

(IIIa R = H)
(IIIb R = Bn)

The compounds of the formulae (IIIa) and (IIIb) are characterized by three chiral carbon atoms each with S-configuration. Prior art preparations of these compounds are mainly based on non-enantioselective methods and subsequent racemate resolutions, either by crystallizations with chiral acids or by enantioselective enzymatic hydrolysis of appropriate derivatives. For example, a published procedure from G. C. Malakondaiah et al. in Synthetic Communications 38, 1737-1744 (2008) uses L(+)-mandelic acid to resolve a racemic mixture of compound (IIIb).

In U.S. Pat. No. 8,119,375 (Sanofi-Aventis) a method for the preparation of compound (IIIa) is disclosed which comprises the enantioselective hydrolysis of 3-(2-oxo-cyclopentyl)-2-phenylacetylamino-propionic acid under the influence of penicillin G amidase. Both methods are suffering from the disadvantage to transform about half of the quantity of the precursor material into undesired isomers which are waste or must be isomerized for recycling.

Another prior art method disclosed in published application No. US 2011/0257408 A1 (Chiral Quest Inc.) employs an asymmetric hydrogenation procedure to produce optically pure substituted alanines by using certain complex precious metal catalysts, for instance the chiral phosphine catalysts [Rh(COD)(ScRp-DuanPhos)]$BF_4$ or [Rh(COD)(RcSp-DuanPhos)]$BF_4$. This method is suffering from several major disadvantages including the high cost and limited availability of such precious metal phospine catalysts and the notorious practical problems associated with the removal of the residual metal and phoshane ligands during the production of the pharmaceutical ingredient.

Another prior art multistep asymmetric synthesis of (2S,3aS,6aS)-cyclopenta[b]pyrrole-2-carboxylic acid benzyl ester (IIIb) from cyclopentanone via a SAMP-hydrazone has been described by G. C. M. Kondaiah et al., Synthetic Communications 41, 1186-1191, 2011. However, this synthesis is not applicable to an industrial scale because the chiral auxiliary SAMP-hydrazone is a highly prized compound which is not available in commercial quantities.

For the industrial large scale preparation of the compounds of the formulae (IIIa) and (IIIb) and, finally, of Ramipril, a preferred process should involve a minimum number of reaction steps which proceed in high yields and high selectivity and which are starting from readily available and cheap raw materials to provide the desired compound with high purity. Safety, environmental compatibility and cost of processing and reagents are further major requirements.

Thus, the problem to be solved by the present invention is to establish an improved process for the preparation of compounds (IIIa) and (IIIb) which avoids aforesaid disadvantages associated with racemate resolutions and precious metal catalyzed reactions, and which proceed with high efficiency, high yield and selectivity to provide the desired products.

The above problem has been solved by providing an improved process including new compounds with a defined stereochemistry at the beginning of the synthesis and keeping the stereochemistry throughout the synthesis as further described below.

In one embodiment the present invention relates to a process for the preparation of the compound of formula (I)

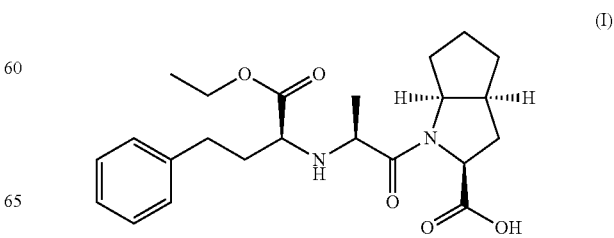

comprising the steps of
(A) reacting a chiral amine of the formula (IV)

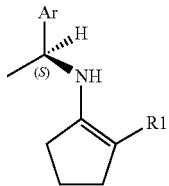
(IV)

wherein
R¹ is CO$_2$—R⁴ or CN;
R⁴ is (C1-C4)alkyl;
Ar is phenyl, optionally substituted by one, two or three substituents selected, independently of each other, from halogen, (C1-C4)alkoxy and (C1-C4)alkyl), or 1-naphtyl;
with an 2-acylamino-acrylic acid ester of the formula (V)

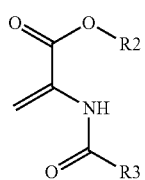
(V)

wherein
R² is (C1-C4)alkyl;
R³ is hydrogen,
(C1-C4)alkyl, wherein optionally one, two or three hydrogen atoms may be replaced by fluorine,
(C1-C4)alkoxy, or
phenyl;
to give the chiral imine of the formula (VI),

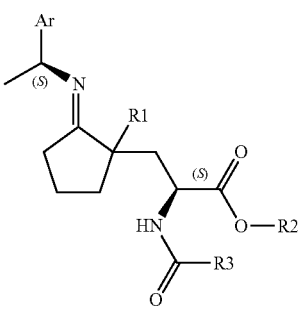
(VI)

wherein
R¹ is CO$_2$R⁴ or CN;
R² is (C1-C4)alkyl;
R³ is (C1-C4)alkyl, wherein optionally one, two or three hydrogen atoms may be replaced by fluorine,
(C1-C4)alkoxy, or
phenyl;
R⁴ is (C1-C4)alkyl; and
Ar is phenyl, optionally substituted by one, two or three substituents selected, independently of each other, from halogen, (C1-C4)alkoxy and (C1-C4)alkyl), or is 1-naphtyl;
with the exception that, if R³ is H in a compound of formula (V), the bicyclic compound of formula (VI') is prepared,

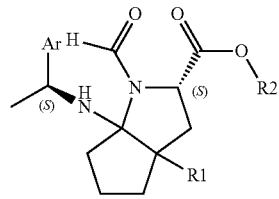
(VI')

wherein
R¹ is CO$_2$R⁴ or CN;
R² is (C1-C4)alkyl;
R⁴ is (C1-C4)alkyl;
Ar is phenyl, optionally substituted by one, two or three substituents selected, independently of each other, from halogen, (C1-C4)alkoxy and (C1-C4)alkyl, or is 1-naphtyl; and, either,
B-1a) hydrolysing the chiral imine in a compound of formula (VI)
or hydrolysing the amine in a bicyclic compound of formula (VI'), respectively, preferably with a mild aqueous acid treatment, to give either the chiral ketone of formula (VII),

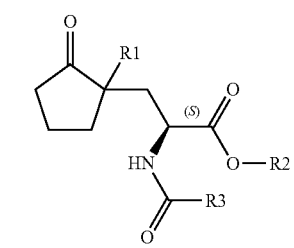
(VII)

wherein
R¹ is CO$_2$R⁴ or CN;
R² is (C1-C4)alkyl;
R³ is (C1-C4)alkyl, wherein optionally one, two or three hydrogen atoms may be replaced by fluorine,
(C1-C4)alkoxy, or
phenyl;
R⁴ is (C1-C4)alkyl;
or to give the bicyclic compound of formula (VII'), respectively,

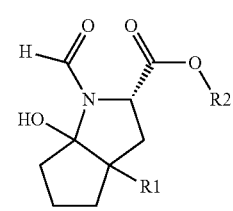
(VII')

wherein
R¹ is CO$_2$R⁴ or CN;
R² is (C1-C4)alkyl, and
R⁴ is (C1-C4)alkyl;
followed by
(B-1b) hydrolysing the chiral ketone of formula (VII),
or hydrolysing the bicyclic compound of formula (VII'), preferably by treating with a strong aqueous acid, to give the chiral amino acid of the formulae (VIII) or a salt thereof,

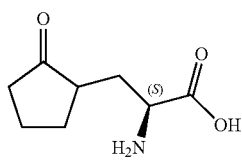
(VIII)

which is in equilibrium with the chiral bicyclic amino acid of the formula (IX) or a salt thereof

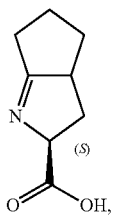
(IX)

or, alternatively, (B-2) hydrolysing the chiral imine of the formula (VI), or hydrolysing the bicyclic compound of the formula (VI'), respectively, preferably with a strong aqueous acid, to give directly the chiral amino acid of formula (VIII) or a salt thereof,

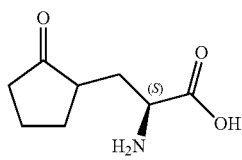
(VIII)

which is in equilibrium with the chiral bicyclic amino acid of the formula (IX) or a salt thereof

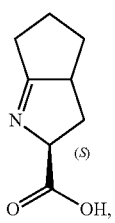
(IX)

and (C) converting the compound (IX) or a salt thereof from the mixture of the compounds (VIII) and (IX) or a salt thereof by catalytic hydrogenation into the compound of the formula (IIIa) or a salt thereof

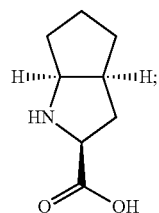
(IIIa)

and (D) converting the compound of formula (IIIa) into ramipril (I).

In an embodiment of the process step D), the compound of formula (IIIa) or a salt thereof is converted into ramipril (I) by (D-1) reacting the compound of formula (IIIa)

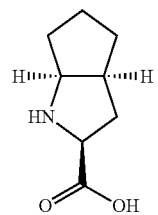
(IIIa)

with a compound of formula (X)

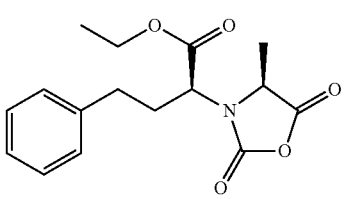
(X)

to give the compound of formula (I)

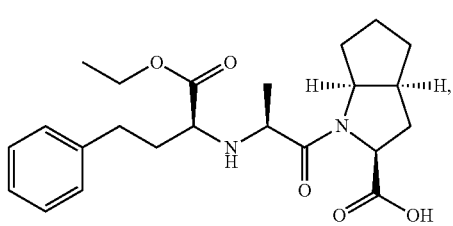
(I)

or, alternatively, (D-2a) reacting compound (IIIa) with benzyl alcohol to give a compound of formula (IIIb) or a salt thereof

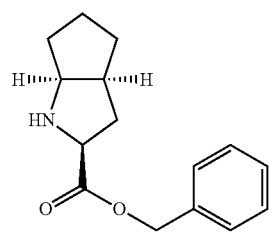
(IIIb)

and then (D-2b-1) reacting the compound of formula (IIIb) with the compound of formula (X) to give a compound formula (XI),

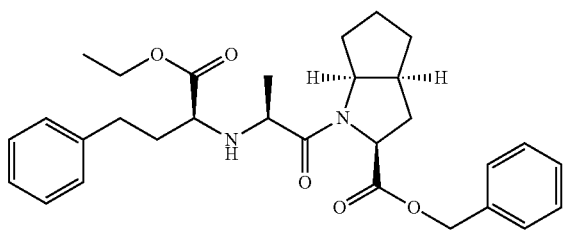

(XI)

or, alternatively, (D-2b-2) reacting the compound of formula (IIIb) with the compound of formula (II)

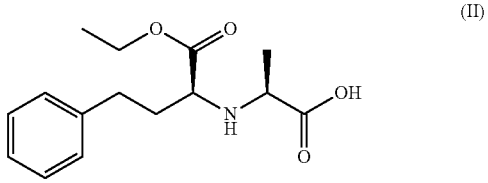 [SMILES: CCOC(=O)[C@H](CCc1ccccc1)N[C@@H](C)C(=O)O]

(II)

in the presence of a coupling reagent to give a compound of formula (XI), and (D-2c) forming the compound of formula (I) from the compound of formula (XI) by catalytic hydrogenation.

"(C1-C4)alkyl" means a linear or branched alkyl group such as methyl, ethyl, propyl, isopropyl, n-butyl, iso-butyl and tert.-butyl.

"(C1-C4)alkoxy" means methoxy, ethoxy, propoxy, iso-propoxy, n-butoxy, iso-butoxy, and tert.-butoxy.

"Halogen" means fluorine, chlorine, or bromine.

In one embodiment of the process of the invention R2 in any one of the compounds of formulae (V), (VI), (VI'), (VII) and (VII') is methyl or ethyl. In another embodiment R2 is methyl.

In one embodiment of the process of the invention R3 in the compound of formula (V) is H, methyl, ethyl, propyl, butyl, trifluoromethyl, methoxy, ethoxy, propoxy, butoxy, or phenyl. In another embodiment R3 is H, methyl, trifluoromethyl or methoxy. In another embodiment R3 is methyl, trifluoromethyl or methoxy. In another embodiment R3 is methyl.

In one embodiment of the process of the invention R3 in any one of the compounds of formulae (VI) and (VII) is methyl, ethyl, propyl, butyl, trifluoromethyl, methoxy, ethoxy, propoxy, butoxy, or phenyl. In another embodiment R3 is methyl, trifluoromethyl or methoxy. In another embodiment R3 is methyl.

In one embodiment of the process of the invention R4 in any one of the compounds of formulae (IV), (VI), (VI'), (VII) and (VII') is methyl or ethyl. In another embodiment R4 is methyl.

In one embodiment of the process of the invention "Ar" in any one of the compounds of formulae (IV), (VI), and (VI') is phenyl, 4-methoxyphenyl, 4-chlorophenyl or naphtyl. In a further embodiment "Ar" is phenyl.

The present invention further relates to each of the process steps (A), steps (B-1a) and (B1-b), and step (B-2), respectively, and to the compounds used as intermediates in these steps for the synthesis of a compound of formula (IIIa) or (IIIb) and finally ramipril.

In the following the various aspects of the invention are described in more detail. In the following the preparation and reaction of the compounds of formula (IV), (VI), (VI'), (VII) and (VII') is described including each of the various embodiments (IVa), (IVb), (VIa), (VIb), (VIa'), (VIb'), (VIIa), (VIIb), (VIIa') and (VIIb'), respectively.

In one embodiment of the process of the invention R1 in any one of the compounds of formulae (IV), (VI), (VI'), (VII) and (VII') is $CO_2R^4$ (designated as formulae (IVa), (VIa), (VIa'), (VIIa) and (VIIa'), respectively). In another embodiment, R1 in any one of the compounds of formulae (IV), (VI), (VI'), (VII) and (VII') is CN (designated as formulae (IVb), (VIb), (VIb'), (VIIb) and (VIIb'), respectively).

As mentioned above the present invention further relates to process step A), which is a process for the preparation of the chiral imine of the formula (VI)

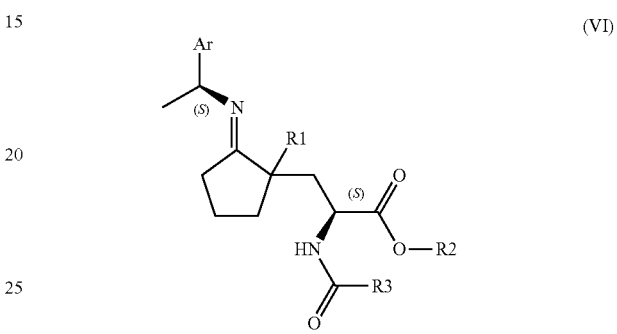

(VI)

wherein
  $R^1$ is $CO_2R^4$ or CN;
  $R^2$ is (C1-C4)alkyl;
  $R^3$ is (C1-C4)alkyl, wherein optionally one, two or three hydrogen atoms may be replaced by fluorine,
    (C1-C4)alkoxy, or
    phenyl;
  $R^4$ is (C1-C4)alkyl; and
  Ar is phenyl, optionally substituted by one, two or three substituents selected, independently of each other, from halogen, (C1-C4)alkoxy and (C1-C4)alkyl), or is 1-naphtyl;
or the bicyclic compound of formula (VI'),

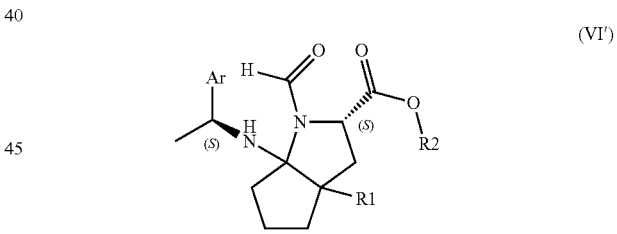

(VI')

wherein
  $R^1$ is $CO_2R^4$ or CN;
  $R^2$ is (C1-C4)alkyl;
  $R^4$ is (C1-C4)alkyl;
  Ar is phenyl, optionally substituted by one, two or three substituents selected, independently of each other, from halogen, (C1-C4)alkoxy and (C1-C4)alkyl, or is 1-naphtyl;
comprising
  (A) reacting a chiral amine of the formula (IV)

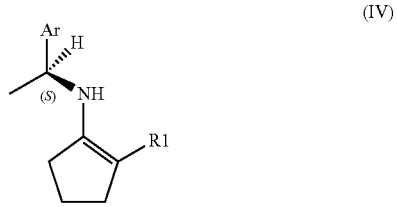

(IV)

wherein

R¹ is CO₂—R⁴ or CN;

R⁴ is (C1-C4)alkyl;

Ar is phenyl, optionally substituted by one, two or three substituents selected, independently of each other, from halogen, (C1-C4)alkoxy and (C1-C4)alkyl), or 1-naphtyl;

with a 2-acylamino-acrylic acid ester of the formula (V)

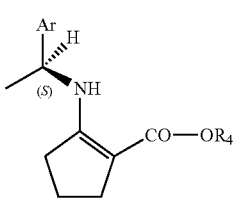

(V)

wherein

R² is (C1-C4)alkyl;

R³ is hydrogen (for obtaining a compound of VI'), or

R3 is (C1-C4)alkyl, wherein optionally one, two or three hydrogen atoms may be replaced by fluorine, (C1-C4)alkoxy, or Phenyl (for obtaining a compound of formula (VI).

In process step A) a compound of formula (IV) is used as starting material. In particular a compound of formula (IV), wherein R1 is COOR4, is used. This is a compound of formula (IVa)

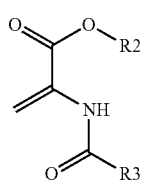

(IVa)

wherein Ar is phenyl optionally substituted by one, two or three substituents selected, independently of each other, from halogen, (C1-C4)alkoxy and (C1-C4)alkyl), or is 1-naphtyl and R⁴ is (C1-C4)alkyl.

The 2-oxo-cyclopentane-carboxylic acid alkyl esters used for preparing the 2-[(S)-1-aryl-ethylamino]-cyclopent-1-ene-carboxylic acid esters of the formula (IVa) are commercially available or can be obtained by procedures known in the art such as by making the ester from the commercially available carboxylic acids. The acids can also be prepared by methods known in the art.

The 2-[(S)-1-aryl-ethylamino]-cyclopent-1-ene-carboxylic acid esters of the formula (IVa), in which R⁴ is (C1-C4)alkyl, especially methyl or ethyl, are prepared from compounds which are available in commercial quantities, e.g. as outlined in scheme 1 for Ar=phenyl: The reaction of the 2-oxo-cyclopentane-carboxylic acid ethyl ester and (S)-1-phenyl-ethylamine, as described by literature procedures, for example in S. H. Gellman, J. Org. Chem. 2001, 66, 5629-5632, provide the enaminoesters (IVa) in high yield. Similar other 2-oxo-cyclopentane-carboxylic acid alkyl esters can be used.

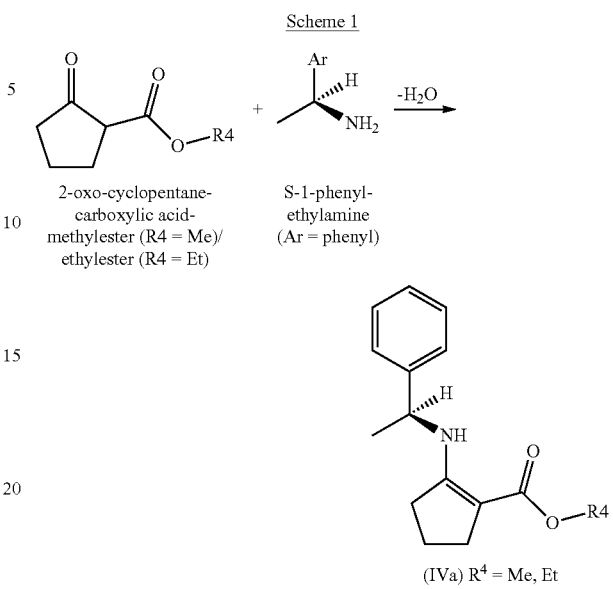

Scheme 1

2-oxo-cyclopentane-carboxylic acid-methylester (R4 = Me)/ ethylester (R4 = Et)

S-1-phenyl-ethylamine (Ar = phenyl)

(IVa) R⁴ = Me, Et (S)-1-phenyl-ethylamine represents only one compound selected from a large variety of possible chiral amines which are produced at several thousand tons scale by commercial suppliers, e.g. by BASF corporation (Trademark ChiPros®; Chimica Oggi 27(5), September-October 2009). Typical examples for substituted (S)-1-phenyl-ethylamines that can be used according to the present invention include for example (S)-1-(4-methoxy-phenyl)-ethylamine, (S)-1-(3-methoxyphenyl)-ethylamine, (S)-1-(2,4-dichlorophenyl)-ethylamine, (S)-1-(4-methylphenyl)-ethylamine and (S)-1-(1-naphtyl)-ethylamine. These compounds are commercially available or can be prepared by known procedures such as described by M. Breuer, K. Ditrich et al., Angew. Chem. Int. Ed. 43(7), 788-824 (2004).

In another aspect of process step (A) a compound of formula (IV), wherein R1 is CN, is used as starting material. This is a compound of formula (IVb)

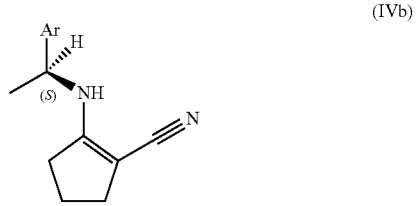

(IVb)

wherein

Ar is phenyl optionally substituted by one, two or three substituents selected, independently of each other, from halogen, (C1-C4)alkoxy and (C1-C4)alkyl), or is 1-naphtyl. This compound itself is a further embodiment of the present invention.

The new 2-[(S)-1-aryl-ethylamino]-cyclopent-1-ene-carbonitriles of formula (IVb) are provided in a similar manner from 2-oxo-cyclopenane-carbonitrile, e.g. as outlined in scheme 2 for Ar=phenyl.

Scheme 2

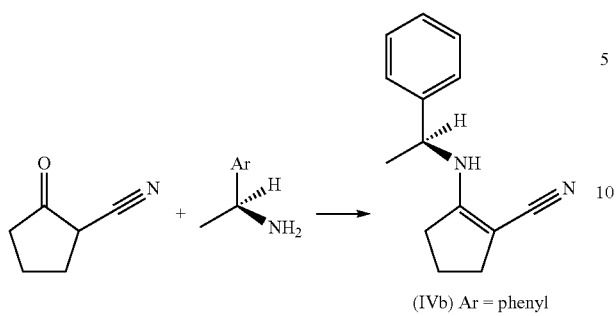

(IVb) Ar = phenyl

The starting material 2-oxo-cyclopenane-carbonitrile is commercially available or it can be prepared from cheap adiponitrile, for example as described by H.-J. Liu et al. in Tetrahedron 59, 1209-1226 (2003).

In another embodiment the present invention relates to a compound of the formula (VI)

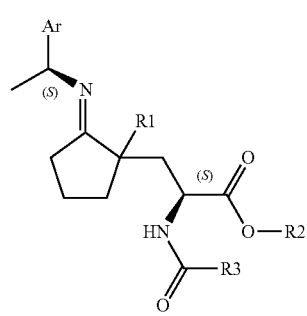

(VI)

wherein
$R^1$ is $CO_2R^4$ or CN;
$R^2$ is (C1-C4)alkyl;
$R^3$ is (C1-C4)alkyl, wherein optionally one, two or three hydrogen atoms may be replaced by fluorine,
(C1-C4)alkoxy, or
phenyl;
$R^4$ is (C1-C4)alkyl;
Ar is phenyl optionally substituted by one, two or three substituents selected, independently of each other, from halogen, (C1-C4)alkoxy and (C1-C4)alkyl) or is 1-naphtyl.

In one embodiment of a compound of formula (VI) the present invention relates to the compound of formula (VIa)

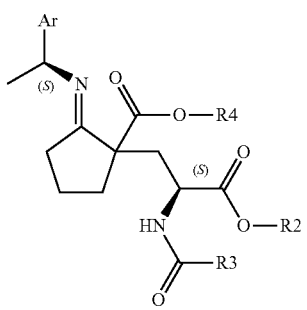

(VIa)

wherein
$R^2$ is (C1-C4)alkyl;
$R^3$ is (C1-C4)alkyl, wherein optionally one, two or three hydrogen atoms may be replaced by fluorine,
(C1-C4)alkoxy, or
phenyl;
$R^4$ is (C1-C4)alkyl; and
Ar is phenyl optionally substituted by one, two or three substituents selected, independently of each other, from halogen, (C1-C4)alkoxy and (C1-C4)alkyl) or is 1-naphtyl.

In a further embodiment of a compound of formula (VI) the present invention relates to a compound of the formula (VIb),

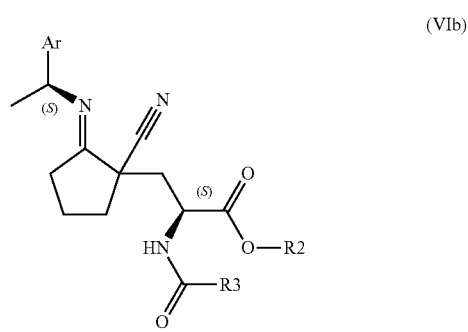

(VIb)

wherein
$R^2$ is (C1-C4)alkyl;
$R^3$ is (C1-C4)alkyl, wherein optionally one, two or three hydrogen atoms may be replaced by fluorine,
(C1-C4)alkoxy, or
phenyl;
$R^4$ is (C1-C4)alkyl; and
Ar is phenyl, optionally substituted by one, two or three substituents selected, independently of each other, from halogen, (C1-C4)alkoxy and (C1-C4)alkyl), or is 1-naphtyl.

In a further embodiment of a compound of formula (VI) the carbon atom bearing the R1 group has the (S) configuration. Accordingly, in this embodiment, each of the compounds of formula (VIa) or (VIb) has also the (S)-stereochemistry at the carbon bearing the R1 group (see scheme 3). These are compounds having the (S,S,S) stereochemistry at all three chiral carbon atoms.

The compounds of formula (VI), incl. (VIa) and (VIb), are prepared in reaction step (A). Step (A) is carried out by mixing the 2-acylamino-acrylic ester of the formula (V) with the compound of formulae (IVa) or (IVb), respectively, either without any solvent or in the presence of an inert organic solvent, and heating the mixture at an appropriate temperature. Suitable inert organic solvents that can be used are, but are not limited to, acetonitrile, acetone, dioxane, dichloromethane, chloroform, methyl-tert.-butylether, n-butyl-acetate, ethyl acetate, methyl-isobutyl-ketone, tetrahydrofuran or 2-methyl-tetrahydrofuran. The temperature of the reaction mixture is kept in a range of 0° C. to 100° C., preferably in a range of 40° C. to 80° C. The reaction can be followed by liquid chromatography.

The 2-acylamino-acrylic esters of the formula (V) are commercially available or can be prepared from the corresponding serine-esters by methods known in the art. For instance, the preparation of 2-acetylamino-acrylic acid-methylester is described in WO2009/098251 (DSM). The respective ethylester can be prepared by esterification of 2-acetylamino-acrylic acid according to R. A. Hughes et al., J. Am. Chem. Soc., 127(44), 15644-15651, (2005). The 2-formamido-acrylic acid-methylester can be prepared in one step from serine-methylester according to L. Panella et al., J. Org. Chem., 71, 2026-2036 (2006). Preparation of the 2-trifluoroacetylamino-acrylic acid-methylester is described for instance by A. Avenoza et al., New Journal of Chemistry, 31, 224-229 (2007) and of the 2-methoxycarbonylaminoacrylic acid-methylester by Y. Torisawa, J. Org. Chem., 57, 5741-5747 (1992).

Surprisingly, step (A) of the process of the present invention, namely the reaction of chiral enaminoesters (IVa) or of the chiral enaminocarbonitriles (IVb) with 2-acylaminoacrylic esters of the formula (V), delivers the addition products (VI) in a highly stereospecific manner, in particular with regard to the desired S-configuration at the carbon atom bearing the acylamino group (—NHCOR3). In addition, the newly constructed quaternary carbon atom in products of formulae (VIa) and (VIb) is also formed predominantly in one distinct stereoform.

The addition of chiral enamines derived from unsubstituted acyclic beta-ketoesters to 2-acetylamino-acrylic acid-methylester (formula V, $R^2=R^3=Me$) has been described in the literature. According to C. Cave et al. in Tetrahedron Lett. 38 (50), 8703-8706 (1997), this addition reaction proceeds with a diastereomeric excess (de) of >95% with respect to the carbon atom bearing the acetylamino group. Similar results were obtained with chiral enamines derived from alpha-substituted acyclic beta-ketoesters by F. Hendra et al., Tetrahedron Asymmetry 15, 1027-1032 (2004).

In contrast, the addition of 2-acylamino-acrylic esters of the formula (V) to chiral enamines, derived from cyclic beta-ketoesters of the formula (IVa), or to chiral enamines, derived from beta-keto nitriles of the formula (IVb), respectively, as described in the present invention, has not yet been reported.

It has now been found that the reaction of cyclic-beta-ketoesters with chiral enamines in step A) of the process of the present invention can be performed with high yield and, additionally, that compounds of formula (VII) are obtained having the necessary stereochemistry of the amino-function, to obtain, after some transformation, the desired compound (VIII) with the required stereochemistry.

This is surprising since C. Cave et al. and F. Hendra et al. performed their reactions of enamines derived from unsubstituted acyclic beta-ketoesters to 2-acetylamino-acrylic acid-methylester by heating at ca. 60° C. in tetrahydrofuran solution at up to ca. 1 molar concentrations and in 65-75% isolated yield.

However, under the same dilute reaction conditions, the enamines (IV), which are derived from the cyclic beta-ketoesters, did not give any synthetically useful turnover while treated with acrylates of the formula (V) at reflux temperature of the THF solvent. Only traces of the desired products of formulae (VIa) or (VIb) could be detected by HPLC chromatography. Thus, the enamines (IV), which are derived from cyclic beta-ketoesters, would appear to be not suitable for such kind of reaction.

This negative finding is well in accord with results published by S. Delarue-Cochin, J. Org. Chem. 2010, 75, 7596-7604, who investigated the conditions and yield of the reaction of the enamine of ethyl-2-fluoro-beta-keto-butyrate. The results were concentration-dependent (diluted to neat), but independent of the solvent itself. The yield was lowest (38%) at 150° C. without solvent (neat) and varied from 60% (0.8 molar in THF) to 86% (0.2 molar in THF).

It has now been found that the enamines (IV), being derived from the sterically more hindered cyclic beta-ketoesters indeed give a synthetically useful turnover while reacting with acrylates, especially if the reaction conditions are properly chosen. In particular and in contrast to aforesaid results, reaction turnover and final isolated yield significantly increase up to 60-70% if the amount of solvent is reduced (down to neat). Therefore, in one embodiment of the process of the present invention, the reaction of enamines (IV) with acrylates (V) is preferably conducted almost without a solvent. The reaction proceeds the faster the less solvent is used. Advantageously, a volatile solvent is chosen which can be evaporated as the reaction proceeds and stays homogeneous. Some solvent may be used in the beginning to bring both reaction partners physically into close contact in particular if one of them or both are solids. This solvent can be removed by evaporation in the initial phase of the reaction.

Only one distinct stereoisomer of the products of the formulae (VIa) and (VIb) is formed predominantly, whereof typical examples exhibit the absolute stereochemistry as drawn in scheme 3. The configurations of these representative products of compounds of formulae (VIa) and (VIb) have been confirmed unambiguously by single crystal X-ray crystallographic analysis. In particular, the X-ray data are confirming the desired S-configuration of the carbon atom bearing the acylamino group.

Scheme 3

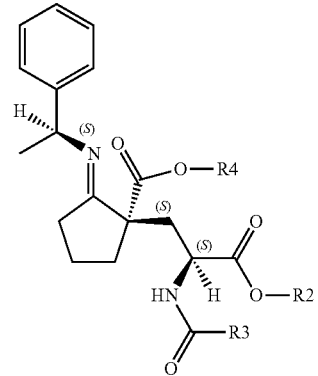

(VIa)

$R^2 = Et, R^3 = Me, R^4 = Et$

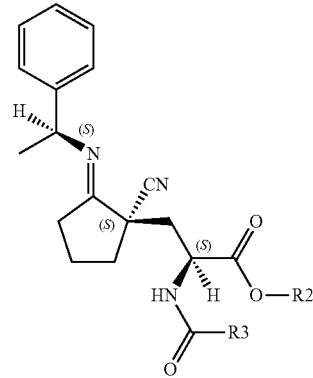

(VIb)

$R^2 = Me, R^3 = Me$

The absolute configuration of the newly formed quaternary carbon atom is in accord with previous results obtained from similar reactions of chiral enaminoesters of cycloalkanones with electrophilic alkenes, for example as described in WO85/04873. The configuration of this quaternary carbon atom is only of limited relevance with regard to the present invention, since it will be destroyed in the subsequent hydrolysis/decarboxylation steps (B1) or (B-2) (see below).

However, the predominant formation of both newly constructed chiral centers—as drawn in scheme 3—delivers the diasteromerically enriched intermediates of the formulae (VIa) and (VIb). Obtaining these intermediates diasteromerically enriched is facilitating their purification, if required, e.g. by crystallization, thus providing a compound with a high stereochemical purity on the amino function which is needed in the next steps.

In another embodiment the present invention relates to a compound of the formula (VI')

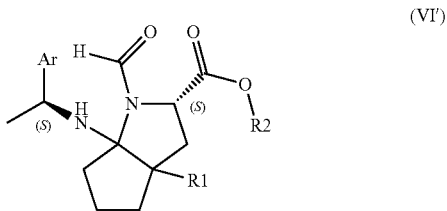

(VI')

wherein
R$^1$ is CO$_2$R$^4$ or CN;
R$^2$ is (C1-C4)alkyl;
R$^4$ is (C1-C4)alkyl; and
Ar is phenyl optionally substituted by one, two or three substituents selected, independently of each other, from halogen, (C1-C4)alkoxy and (C1-C4)alkyl) or is 1-naphtyl.

In one embodiment of a compound of formula (VI') the present invention relates to the compound of formula (VIa')

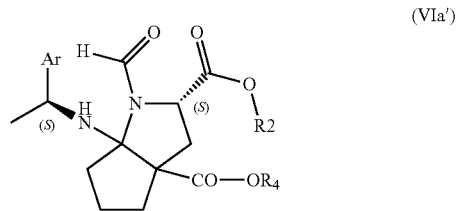

(VIa')

wherein
R$^2$ is (C1-C4)alkyl;
R$^4$ is (C1-C4)alkyl; and
Ar is phenyl optionally substituted by one, two or three substituents selected, independently of each other, from halogen, (C1-C4)alkoxy and (C1-C4)alkyl) or is 1-naphtyl.

In a further embodiment of a compound of formula (VI') the present invention relates to a compound of formula (VIb')

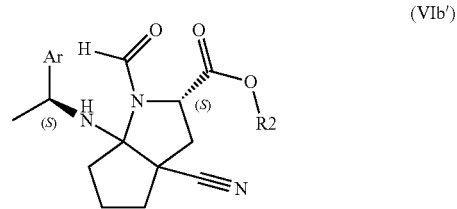

(VIb')

wherein
R$^2$ is (C1-C4)alkyl; and
Ar is phenyl optionally substituted by one, two or three substituents selected, independently of each other, from halogen, (C1-C4)alkoxy and (C1-C4)alkyl) or is 1-naphtyl.

If the residue R$^3$ has the meaning of a hydrogen atom, the following structural anomaly occurs in reaction step (A): In this case the initially formed imines of the formulae (VIa) and (VIb) predominantly cyclise, in an excess of greater than 95%, into the bicyclic compounds of the formulae (VIa') and (VIb'), which are in equilibrium with the open forms (VIa) and (VIb), respectively (scheme 4). This distinctive structural feature is evident from the nuclear magnetic resonance analysis of these compounds. However, this has no impact on their utility for using them as well as intermediates for the preparation of the intermediate of formula (IIIa) and finally of ramipril according to the process of the present invention since both forms of these compounds can be hydrolysed into a compound of formula (VIII).

Scheme 4

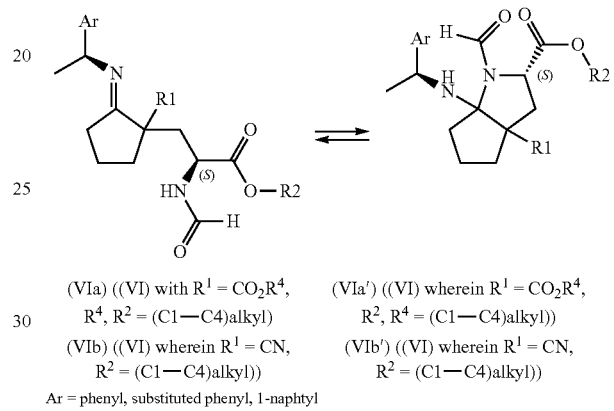

(VIa) ((VI) with R$^1$ = CO$_2$R$^4$, R$^4$, R$^2$ = (C1—C4)alkyl)
(VIb) ((VI) wherein R$^1$ = CN, R$^2$ = (C1—C4)alkyl))
(VIa') ((VI) wherein R$^1$ = CO$_2$R$^4$, R$^2$, R$^4$ = (C1—C4)alkyl))
(VIb') ((VI) wherein R$^1$ = CN, R$^2$ = (C1—C4)alkyl))

Ar = phenyl, substituted phenyl, 1-naphtyl

The products of formulae (VIa), (VIb), (VIa') and (VIb') can be isolated and purified, e.g. by crystallization, or they are directly subjected to partial hydrolysis, e.g. with mild aqueous acids (step B-1a).

In another embodiment the present invention relates to a compound of formula (VII)

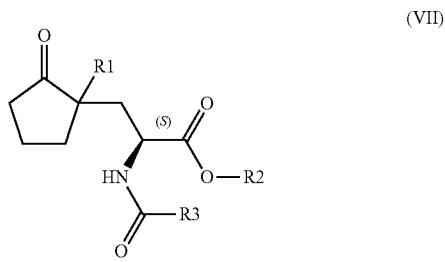

(VII)

wherein
R$^1$ is CO$_2$R$^4$ or CN;
R$^2$ is (C1-C4)alkyl;
R$^3$ is (C1-C4)alkyl, wherein optionally one, two or three hydrogen atoms may be replaced by fluorine,
(C1-C4)alkoxy, or
phenyl;
R$^4$ is (C1-C4)alkyl.

In one embodiment the present invention relates to a compound of formula (VII) wherein R1 is CO2R$^4$ (VIIa)

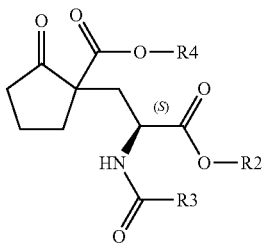

(VIIa)

wherein
R² is (C1-C4)alkyl;
R³ is (C1-C4)alkyl, wherein optionally one, two or three hydrogen atoms may be replaced by fluorine,
(C1-C4)alkoxy, or
phenyl;
R⁴ is (C1-C4)alkyl.

In a further embodiment of a compound of formula (VIIa) the carbon atom bearing the COOR4 group has the (S) stereochemistry. In this embodiment both chiral carbon atoms have the (S,S) stereochemistry (compound of formula (VIIa-1))

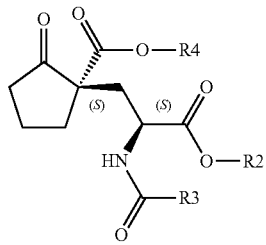

(VIIa-1)

wherein
R² is (C1-C4)alkyl;
R³ is (C1-C4)alkyl, wherein optionally one, two or three hydrogen atoms may be replaced by fluorine,
(C1-C4)alkoxy; or
phenyl;
R⁴ is (C1-C4)alkyl;

In a further embodiment of a compound of formula (VII) the present invention relates to a compound of formula (VIIb)

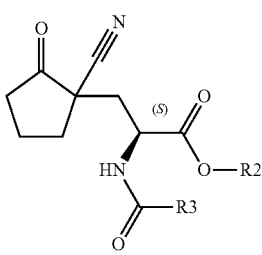

(VIIb)

wherein
R² is (C1-C4)alkyl;
R³ is (C1-C4)alkyl, wherein optionally one, two or three hydrogen atoms may be replaced by fluorine,
(C1-C4)alkoxy, or
phenyl.

In a further embodiment of a compound of formula (VIIb) the carbon atom bearing the CN group has the (R) stereochemistry. This compound has the formula (VIIb-1).

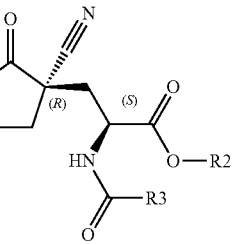

(VIIb-1)

wherein R2 and R3 are as in (VIIb) above.

In another embodiment the present invention relates to a compound of formula (VII')

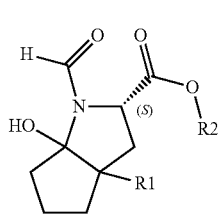

(VII')

wherein
R¹ is CO₂R⁴ or CN and
R² is (C1-C4)alkyl,
R⁴ is (C1-C4)alkyl.

In one embodiment of a compound of formula (VII') the present invention relates to a compound of formula (VIIa')

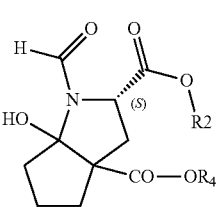

(VIIa')

wherein
R² is (C1-C4)alkyl and
R⁴ is (C1-C4)alkyl.

In a further embodiment of a compound of formula (VII) the present invention relates to a compound of formula (VIIb')

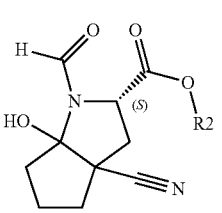

(VIIb')

wherein
R² is (C1-C4)alkyl.

The compounds of formula (VII), incl. (VIIa) and VIIb), as well as of formula (VII'), incl. (VIIa') and (VIIb'), are prepared in reaction step (B-1a).

In one embodiment of the compounds of the present invention R1 in any one of the compounds of formulae (VI), (VI'), (VII), and (VII') is COOR4.

In another embodiment of the compounds of the present invention R1 in any one of the compounds of formulae (VI), (VI'), (VII), and (VII') is CN.

In one embodiment of the compounds of the present invention R2 in any one of the compounds of formulae (VI), incl. (VIa) and (VIb), (VI'), incl. (VIa') and (VIb'), (VII), incl. (VIIa) and (VIIb), and (VII'), incl. (VIIa') and (VIIb'), is methyl or ethyl. In a further embodiment R2 is methyl.

In one embodiment of the compounds of the present invention R3 in any one of the compounds of formulae (VI), incl. (VIa) and (VIb), and (VII), incl. (VIIa) and (VIIb), is methyl, ethyl, propyl, butyl, trifluoromethyl, methoxy, ethoxy, propoxy, butoxy, or phenyl.

In a further embodiment thereof R3 is methyl, trifluoromethyl or methoxy. In a further embodiment R3 is methyl.

In one embodiment of the compounds of the present invention R4 in any one of the compounds of formulae (VI), incl. VIa, (VI'), incl. (VIa), (VII), incl. (VIIa), and (VII'), incl. (VIIa'), is methyl or ethyl. In a further embodiment R4 is methyl.

In one embodiment of the compounds of the present invention "Ar" in any one of the compounds of formulae (IVb), (VI), incl. (VIa) and (VIb), and (VI'), incl. (VIa') and VIb') is phenyl, 4-methoxyphenyl, 4-chlorophenyl or naphtyl. In a further embodiment "Ar" is phenyl.

WO2009/098251 (DSM) describes compounds of formula [1] having the chemical constitution of the compounds of formula (VII) wherein $R^1$ is $CO_2R^4$ with R4 being alkyl esp. ethyl (Ex. 1) but as a undefined mixture of all possible stereoisomers, incl. undefined stereochemistry at the carbon atoms bearing the R1 group as well as the acylamino residue. This mixture is further hydrolyzed to the free amino carboxylic acid followed by further reactions, incl. an enzymatic cleavage, to obtain the compound of formula (VIII) (Ex. 2, 3, and 4). A compound of formula (VII) wherein $R^1$ is $CO_2R^4$ or a compound of formula (VIIa) with the (S) stereochemistry as shown above is not disclosed.

The hydrolysis of the compound of formula (VI) or (VI') to obtain a compound of formula (VII) or (VII'), respectively, may be performed in various ways which are known for a person skilled in the art. Usually this is done using an acid treatment. The identification of such an acid and its combination with the other reactions conditions such as temperature and duration is known to a person skilled in the art.

For example, the hydrolysis may be done with a mild aqueous acid treatment. Appropriate acids that can be used are, but are not limited to, dilute acetic acid, propionic acid, formic acid or dilute hydrochloric acid at a temperature of 20-100° C. The chiral (S)-1-aryl-ethylamines that remain in the acidic aqueous phase can be separated by extraction and recycled. Stronger reaction conditions and acids may likewise be used for the cleavage of the imine in a compound of formula (VI) or the amine in a compound of formula (VI'). However, for a better control of the reaction and avoiding further cleavage of the esters in a compound of formula (VII) or (VII') mild aqueous acid treatment is preferred.

The compounds of the formulae (VIIa), (VIIb), (VIIa') and (VIIb') likewise can be isolated and purified, e.g. by crystallization or chromatography. Subsequently, they are subjected to hydrolysis/decarboxylation, which can be done under heating at 60° C. to 100° C. in strong aqueous acids to produce the amino acid of the formula (VIII) (step B-1b).

Accordingly, the terms mild and strong aqueous acid treatment refer to the overall reaction conditions (acid and temperature used) such that the hydrolysis of the compounds is as desired, especially wherein the imine in a compound of formula (VI) is hydrolysed to a compound of formula (VII) or the amine in a compound of formula (VI') is hydrolysed to obtain a compound of formula (VII'), which is preferably done under mild acid reaction conditions.

Alternatively, the imines of the formulae (VIa) and (VIb) and the bicyclic compounds of the formulae (VIa') and (VIb') can be directly subjected to imine hydrolysis as well as to decarboxylation to produce the chiral S-configurated amino acid of the formula (VIII) (step B-2). This reaction may be done under heating at 60° C. to 100° C. and using strong aqueous acids.

Appropriate strong aqueous acids which can be used in the hydrolysis include hydrochloric acid, hydrobromic acid, sulfuric acid and methanesulfonic acid. Reaction steps B-1b or B-2 both are leading to compound (VIII), which is in equilibrium with the chiral bicyclic acid of the formula (IX) or their respective salts as shown in scheme 5.

Scheme 5

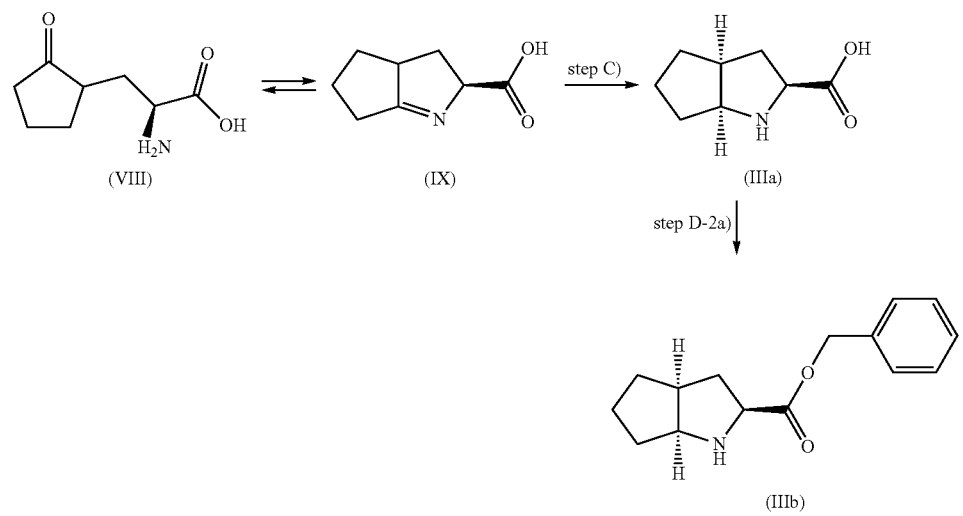

The above-mentioned hydrolysis procedures (steps B-1a, B-1b and B-2) can be applied likewise to the conversion of the N-formyl substituted bicyclic products of the formulae (VIa'), (VIb'), (VIIa') and (VIIb') into the amino acids (VIII) and (IX) via the ketones of the formulae (VIIa) and (VIIb). Nuclear magnetic resonance analysis of the respective intermediates being formed in step B-1a (mild acid hydrolysis) confirmed that the initially formed ketones of the formulae (VIIa) and (VIIb) are predominantly cyclised, in a similar fashion as shown in scheme 4, and also in an excess of greater than 95%, into the bicyclic compounds of the formulae (Vila') and (VIIb') (scheme 6).

Scheme 6

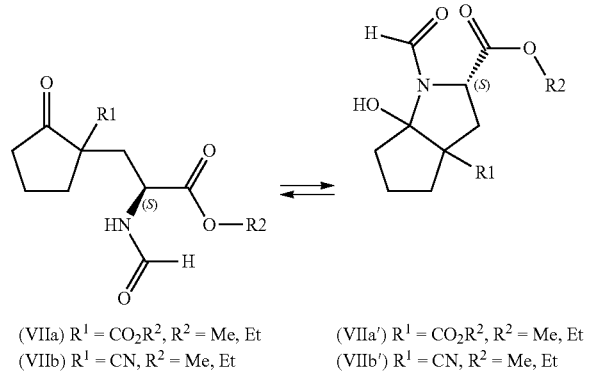

(VIIa) $R^1 = CO_2R^2$, $R^2 = Me, Et$
(VIIb) $R^1 = CN$, $R^2 = Me, Et$ (VIIa') $R^1 = CO_2R^2$, $R^2 = Me, Et$
(VIIb') $R^1 = CN$, $R^2 = Me, Et$

The hydrogenation in step (C) following steps (B-1b) or (B2) may be done stepwise by isolating the intermediates (VIII) and (IX) before hydrogenation is done or hydrogenation may be done in the same reaction vessel without isolating the intermediates (VIII) and (IX) before.

Catalytic hydrogenation of the mixture of compounds (VIII) and (IX) to obtain compound (IIIa) is performed under known standard conditions, preferably by using palladium on charcoal as catalyst in an aqueous solution (step C).

For example, the aqueous phase of the working up of step (B-1b) or (B-2) containing the compound of the formula (VIII) or a salt thereof mixed with the compound (IX) or a salt thereof is admixed with a suitable catalyst. An example of a suitable catalyst is platinum on activated carbon or palladium on activated carbon, and palladium on activated carbon is particularly suitable. A ratio by weight of palladium to activated carbon of from 5:95 to 10:90 is preferred. The amount of catalyst employed per gram of aqueous solution is preferably 1-10 mg. Further activated carbon can be added to the reaction mixture, preferably 5 to 20 weight units per weight unit of catalyst. The hydrogenation is carried out under a hydrogen pressure of from 5 to 15 bar, preferably from 8 to 12 bar. The reaction temperature can be between 40° C. and the boiling point of the reaction mixture, and is preferably 60-100° C.

Compound (IIIa) can optionally be isolated. The compound (IIIa) can be isolated in free form or in the form of an acid addition salt, for example as salt of HCl, HBr, $H_2SO_4$, methanesulfonic acid, toluenesulfonic acid or phenylsulfonic acid.

In one embodiment, the hydrolysis step (B-1b) can be combined together with the hydrogenation step (C) in one reaction vessel to produce compound (IIIa) (designated as step B-1b+C). In another embodiment steps (B-2) and (C) may also be combined in one vessel. In this case the chiral amine resulting from the initial hydrolysis of compounds of formula (VI) or (VI'), is not recycled.

Compound (IIIa) can be converted into ramipril (I) by methods known in the art (step D) which incl. either step D-1) or steps D-2a) and D-2b-1) and D-2c) or steps D-2a) and D-2b-2) and D-2c). This kind of conversion is described e.g. in U.S. Pat. No. 8,119,375. In a first reaction compound (IIIa) can be directly coupled with compound (X)

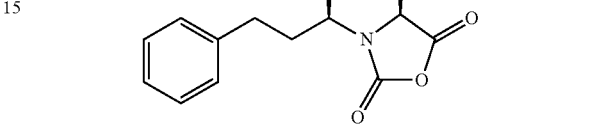

to give Ramipril (I) (step D-1), for example as described in U.S. Pat. No. 8,119,375 B2 (Sanofi-Aventis) and in the Examples below.

Alternatively, compound (IIIa) is transformed into its benzyl ester of formula (IIIb) (step D-2a) by known methods, which reacts directly with the compound of formula (X) to give the Ramipril-benzylester of formula (XI) (step D-2b-1) or, alternatively, by reacting benzylester (IIIb) with the compound of formula (II) in presence of a coupling reagent to provide Ramipril-benzylester (XI) (step D-2b-2).

The amide formation in step (D-2b-2) can be carried out by known methods, for example as described in European patent application EP 79022 A2, example I (4). The compound of the formula (IIIb) is coupled with the compound of the formula (II) in a suitable inert solvent, for example ethyl acetate, butyl acetate, dichloromethane or dimethylformamide, at a temperature of 5-20° C., preferably 10-15° C., in the presence of one or more standard amide-coupling reagents, for example dicyclohexylcarbodiimide, HOBt, propanephosphonic anhydride or methanephosphonic anhydride, keeping the pH preferably at between 8 and 9, for example by means of sodium hydroxide solution. Alkane phosphonic acid anhydrides as coupling reagents are described in U.S. Pat. No. 5,055,591 B2 (Hoechst).

Another suitable coupling reagent is the Vilsmeier salt of the formula (XII).

For example, the salt (XII) is reacted with the acid of formula (II) at −20° C. to +20° C., preferably at −15° C. to 0° C. in dichloromethane, and the resulting mixture is transferred into a water/dichlormethane mixture containing the benzyl ester of the formula (IIIb) while adjusting the pH at 7.0-8.5 with sodium bicarbonate or dilute sodium hydroxide. The N,N-dimethyl-chloromethyl-iminium chloride (XII) is available from chlorination of cheap N,N-dimethylformamide (DMF) with phosgene, phosphorous pentachloride or thionyl chloride (H. Eilingsfeld et al., Angew. Chem., 72(22), 836 (1960)) or it can be purchased commercially (e.g. Aldrich).

Another option for step D-2b-2 is provided by the acylation of the benzyl ester of formula (IIIb) with the acid chloride hydrochloride of formula (XIII)

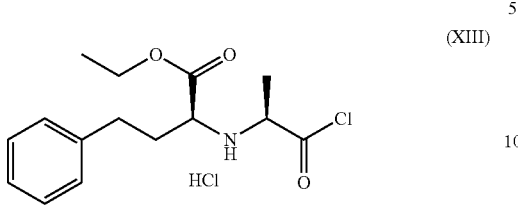

(XIII)

in presence of a base, e.g. triethylamine, as described in published application US 2007/0232680 A1.

compound (XI), benzyl(2S,3aS,6aS)-1-2-[[(1S)-1-(ethoxycarbonyl)-3-phenylpropyl]amino]-(2S)-propanoyl)octahydrocyclopenta[b]pyrrole-2-carboxylate, is optionally isolated before further converting it into (I).

In the final reaction step D-2c) Ramipril (I) is produced by hydrogenation of compound (XI) in the presence of a suitable catalyst such as palladium on active charcoal. Accordingly, the benzyl ester of formula (XI) is cleaved in a suitable solvent, e.g. a ($C_1$-$C_3$)alkanol, preferably methanol or ethanol, at a temperature of 0-20° C., preferably 5-10° C., under a pressure of 0.5-3 bar with addition of a suitable catalyst, e.g. Pd/C (10% by weight).

The compound of formula (I) can optionally be purified further by standard methods following steps (D-1) or (D-2c), for example by chromatographic methods or by recrystallization from a suitable solvent. A suitable solvent for crystallisation is for example a mixture of methanol and diisopropyl ether, or alternatively acetone, or ethyl acetate.

The invention is further described by the following Examples without limiting it to them.

EXAMPLES

Abbreviations ca. circa
h hour(s)
i. vac. in vacuum
LC-MS liquid chromatography-mass spectrometry
M molar
MTBE methyl-tert.-butylether
NMR nuclear magnetic resonance
DCM dichloromethane
Ar aryl
Bn benzyl
Me methyl
Et ethyl The invention is described in more detail by the examples that follow. These examples are designated to illustrate the invention, but do not limit its scope. Each step of the process described in the present invention may be operated either batch by batch or as a continuous process, or semi-continuous mode, and is scalable on larger amounts than described here.

The NMR assignments are for illustration only based on analysis of the one-dimensional and multi-dimensional $^1$H and $^{13}$C NMR spectra as done by those skilled in the art. A more detailed analysis of the spectra may lead to minor reassignments of some NMR peaks, which obviously does not change the overall assignment. NMR spectra were recorded on 500 MHz and on 600 MHz instruments, shifts are relative to TMS in [ppm]; the solvent is always DMSO-$d_6$ if not denoted otherwise.

Preparation of Compounds of Formula (IV) Incl. (IVa) and IVb)

Example 1

2-[(S)-1-phenyl-ethylamino]-cyclopent-1-ene-carbonitrile (compound (IVb) wherein Ar=phenyl)

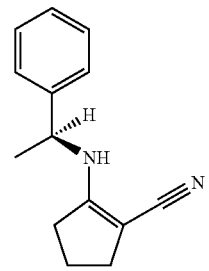 [SMILES: C[C@H](NC1=C(C#N)CCC1)c1ccccc1]

9.80 g (85.3 mmol) of 2-oxo-cyclopentane-carbonitrile (Ark Pharm Inc., purity 95%) were dissolved in 20 ml of toluene and 10.4 g (85.3 mmol) of (S)-1-phenyl-ethylamine (>99%, BASF) were added under cooling at 20° C. to 30° C. After stirring for 4 hours, water and crystals deposited in the reaction vessel, and water was completely removed by distillation with toluene on a rotary evaporator. The remaining crystalline mass was stirred in cold MTBE, filtered and dried to give 16.7 g (92%) of the title product as bright yellow crystals. LC-MS: MH$^+$ 213, $^1$H NMR: 1.39 (d, 3H, Me), 1.72 (m, 2H, H-4), 2.30-2.48 (m, 4H, H-3, H-5), 4.93 (m, 1H, CHN), 7.23 (m, 2H, Ar—H), 7.33 (m, 3H, Ar—H).

Example 2

2-[(S)-1-(4-methoxyphenyl)-ethylamino]-cyclopent-1-ene-carboxylic acid methylester (compound of formula (IV) wherein Ar=4-methoxyphenyl, $R^1$=$CO_2Me$)

10.37 g (70.0 mmol) of 2-oxo-cyclopentane-carboxylic acid methylester (purity 96%, Aldrich) were dissolved in 30 ml of toluene and 10.00 g (65.5 mmol) of (S)-1-(4-methoxyphenyl)-ethylamine (purity>99%, BASF) were stirred under argon for 12 hours at ca. 25° C. Water was completely removed by evaporation of toluene (3×50 ml) and the product was dried at 80° C./1 mbar to give 18.1 g (100%) of the title product as yellow oil.

LC-MS: MH$^+$ 276;

$^1$H NMR: 1.40 (d, 3H, Me), 1.65 (m, 2H, H-4), 2.25, 2.37, 2.62 (3m, 4H, H-3, H-5), 3.57 (s, 3H, $CO_2Me$), 3.73 (s, 3H, OMe), 4.60 (m, 1H, CHN), 6.90, 7.20 (2m, 4H, Ar—H), 7.70 (d, 1H, NH).

Example 3

2-[(S)-1-(1-naphtyl)-ethylamino]-cyclopent-1-ene-carboxylic acid methylester (compound (IV) wherein Ar=1-naphtyl, $R^1$=$CO_2Me$)

The title compound was prepared in an analogous manner as described in Example 2 from 3.89 g (26.3 mmol) of 2-oxo-cyclopentane-carboxylic acid methylester and 4.50 g (25.8 mmol) of (S)-1-(1-naphtyl)-ethylamine (purity 98.5%, BASF) in quantitative yield (7.60 g yellow oil).

LC-MS: MH+ 296;
$^1$H NMR: 1.57 (d, 3H, Me), 1.56, 1.67 (2m, 2H, H-4), 2.05, 2.40, 2.65 (3m, 4H, H-3, H-5), 3.61 (s, 3H, $CO_2Me$), 5.50 (m, 1H, CHN), 6.90, 7.20 (2m, 4H, Ar—H), 7.10-8.20 (m, 7H, ArH).

Example 3a

Preparation of 2-[(S)-1-(phenylethylamino]-cyclopent-1-ene-carboxylic acid methylester (IV) (Ar=4-phenyl, $R^1=CO_2Me$)

The title compound was prepared in an analogous manner as described in Example 2 from 63.51 g (0.43 mol) 2-oxo-cyclopentane-carboxylic acid methylester (purity 96%, Aldrich) and 50.0 g (0.41 mol)(S)-1-phenylethylamine (purity>99%, BASF) in almost quantitative yield (97.0 g, 97%).

LC-MS: MH+ 246; $^1$H NMR: 1.41 (d, 3H), 1.70 (m, 2H), 2.20 (m, 1H), 2.41 (m, 2H), 2.62 (m, 1H), 3.57 (s, 3H), 4.65 (m, 1H), 7.20-7.40 (m, 5H), 7.75 (d, 1H).

Example 4

2-[(S)-1-(4-chlorophenyl)-ethylamino]-cyclopent-1-ene-carbonitrile (compound (IVb) wherein Ar=4-chlorophenyl)

The title compound was prepared in an analogous manner as described in example 1 from 2-oxo-cyclopentane-carbonitrile and (S)-1-(4-chlorophenyl)-ethylamine (purity>98%, BASF): The yield was 94% of bright yellow crystals.

LC-MS: MH+ 247; $^1$H NMR: 1.38 (d, 3H, Me), 1.73 (m, 2H, H-4), 2.30-2.50 (m, 4H, H-3, H-5), 4.92 (m, 1H, CHN), 7.28 (d, 1H, NH), 7.35, 7.40 (2d, 4H, Ar—H).

Preparation of Compounds of Formula (VI), Incl. (VIa) and (VIb)

Example 5

Methyl (2S)-2-acetamido-3-[(1S,2E)-1-cyano-2-[(1S)-1-phenylethyl]imino-cyclopentyl]propanoate (Compound of Formula (VI) (Wherein Ar=Phenyl, $R^1=CN$, $R^2=Me$, $R^3=Me$) from Compound of Formula (IVb) (Wherein Ar=Phenyl, R1=CN) and Compound of Formula (V) (Wherein $R^2=Me$, $R^3=Me$)) (Step A))

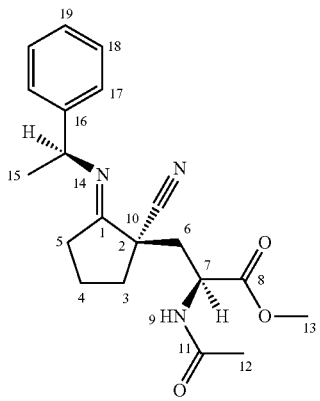

3.00 g (14.13 mmol) of 2-[(S)-1-phenyl-ethylamino]-cyclopent-1-ene-carbonitrile (IVb, Ar=phenyl, Example 1), 2.12 g (14.84 mmol) of 2-acetylamino-acrylic acid-methylester (V, $R^2=Me$, $R^3=Me$) (Aldrich), and 0.05 g of hydroquinone were mixed with 5 ml of acetonitrile and heated under stirring at 65° C. (bath temperature) for 65 hours. The solvent was evaporated and the semi-solid mass was diluted under stirring with 20 ml of MTBE. After cooling to room temperature, the mixture was filtered. The crude solid product was dissolved in a minimum amount of hot dichloromethane and the hot solution was diluted with MTBE. A small amount of solid was removed by filtration. Then the filtrate was evaporated, the residue taken up again in a minimum amount of hot dichloromethane. The vast bulk of dichloromethane then was slowly evaporated using a rotary evaporator while adding successively MTBE. After some time the product separated as sparkling crystals. The suspension was stirred for about two hours while cooling to room temperature. The crystals were filtered, washed with MTBE and dried i.vac. Part of this was used as seeding crystal for making a larger amount of the title compound (see next experiment)

X-ray crystallographic analysis: A specimen was used for the X-ray crystallographic analysis. The X-ray intensity data were measured. The total exposure time was 13.71 hours. The frames were integrated with the Bruker SAINT software package using a narrow-frame algorithm. The integration of the data using an orthorhombic unit cell yielded a total of 7602 reflections to a maximum 8 angle of 69.74° (0.82 Å resolution), of which 2303 were independent (average redundancy 3.301, completeness=63.7%, $R_{int}$=1.71%, $R_{sig}$=1.29%) and 2230 (96.83%) were greater than 2σ($F^2$). The final cell constants of a=9.1247(7) Å, b=11.7442(8) Å, c=18.9593(14) Å, volume=2031.7(3) Å$^3$, are based upon the refinement of the XYZ-centroids of 5717 reflections above 20 σ(I) with 8.857°<2θ<136.6°. Data were corrected for absorption effects using the multi-scan method (SADABS). The ratio of minimum to maximum apparent transmission was 0.859. The structure was solved and refined using the Bruker SHELXTL Software Package, using the space group P 21 21 21, with Z=4 for the formula unit, $C_{20}H_{25}N_3O_3$. The resulting absolute configuration was as drawn above and in Scheme 3.

16.70 g (78.6 mmol) of 2-[(S)-1-phenyl-ethylamino]-cyclopent-1-ene-carbonitrile (IVb, Ar=phenyl, Example 1), 11.82 g (82.6 mmol) of 2-acetylamino-acrylic acid-methylester (V, $R^2=Me$, $R^3=Me$) (Aldrich), and 0.10 g of hydroquinone were mixed with 20 ml of acetonitrile and heated under stirring at 60° C.-65° C. An orange-yellow solution formed within 30 minutes. After ca. 24 hours, a seeding crystal of the title product was added whereupon some product crystallized out. The reaction mixture thickened while most of the solvent was evaporated, and after 48 hours 50 ml of MTBE were added under stirring to the hot suspension. After cooling at room temperature, a first crop of product (12.4 g) was obtained by filtration and washing with MTBE. A second crop (6.00 g) was obtained after a repeated treatment of the concentrated filtrate (without additional acetonitrile and for another 48 hours under the same conditions) to give in total 18.6 g (65%) of the title compound as colorless crystals. The mother liquor still contained the starting compounds and some additional product in a ratio of about 1:1:1 and in principle allowed for a repeated reaction/isolation procedure to obtain a further crop of the title product. (LC peak areas were calibrated).

LC-MS: MH+ 356.
$^1$H NMR: 1.33 (d, 3H, H-15), 1.76, 1.95 (m, 2H, H-4), 1.86 (s, 3H, H-12), 1.95, 2.19 (m, 2H, H-3), 1.92, 2.46 (m,

2H, H-6), 2.45 (m, 2H, H-5), 3.66 (s, 3H, H-13), 4.52 (q, 1H, H-14), 4.59 (m, 1H, H-7), 7.23 (m, 1H, H-19), 7.33 (m, 2H, H-18), 7.37 (m, 2H, H-17), 8.44 (d, 1H, H-9); $^{13}$C NMR: 21.39 (C-4), 22.33 (C-12), 24.04 (C-15), 27.34 (C-5), 34.86 (C-3), 36.55 (C-6), 45.94 (C-2), 49.54 (C-7), 52.08 (C-13), 61.00 (C-14), 120.89 (C-10), 126.29 (C-17), 126.60 (C-19), 128.22 (C-18), 144.89 (C-16), 169.30 (C-11), 171.92 (C-8), 173.31 (C-1).

Example 6

Methyl (2S)-2-acetamido-3-[(1S,2E)-2-[(1S)-1-(4-chlorophenyl)ethyl]imino-1-cyano-cyclopentyl]propanoate (Compound of Formula (VI) (Wherein Ar=4-Chlorophenyl, R$^1$=CN, R$^2$=Me, R$^3$=Me) from Compound of Formula (IV) (Wherein Ar=4-Chlorophenyl, R$^1$=CN) and Compound of Formula (V) (Wherein R$^2$=Me, R$^3$=Me)) (Step A)

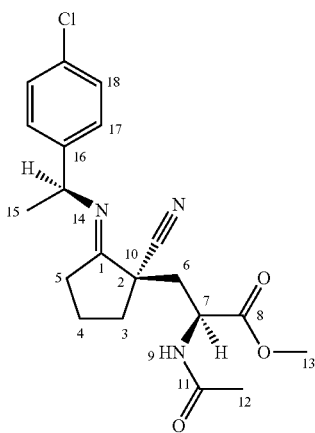

5.00 g (20.3 mmol) of compound (IV) (Ar=4-chlorophenyl, R$^1$=CN, Example 4) and 3.05 g (21.3 mmol) of compound (V) (R$^2$=Me, R$^3$=Me) were converted in an analogous manner as described in Example 5, using 10 ml of MTBE as a solvent, into 5.05 g (63%) of the title compound (yellow solid).

LC-MS: MH$^+$ 390

$^1$H NMR: 1.32 (d, 3H, H-15), 1.75, 1.94 (m, 2H, H-4), 1.86 (s, 3H, H-12), 1.95, 2.20 (m, 2H, H-3), 1.90, 2.45 (m, 2H, H-6), 2.46 (m, 2H, H-5), 3.67 (s, 3H, H-13), 4.53 (q, 1H, H-14), 4.60 (m, 1H, H-7), 7.33-7.46 (m, 4H, H-17, H-18), 8.43 (d, 1H, H-9)

Example 7

Methyl (1S,2E)-1-[(2S)-2-acetamido-3-methoxy-3-oxo-propyl]-2-[(1S)-1-phenylethyl]imino-cyclopentanecarboxylate (compound (VI) (wherein Ar=phenyl, R$^1$=CO$_2$Me, R$^2$=Me, R$^3$=Me) from compound (IV) (wherein Ar=phenyl, R$^1$=CO$_2$Me) and compound (V) (wherein R$^2$=Me, R$^3$=Me)) (step A)

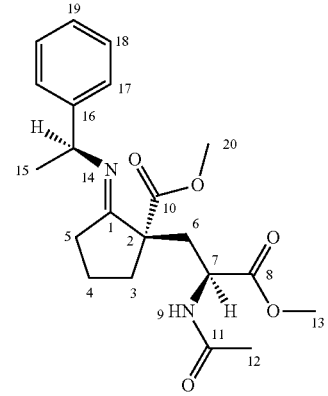

20.00 g (81.53 mmol) (2-[(S)-1-phenyl-ethylamino]-cyclopent-1-ene-carboxylic acid methylester (IV) (Ar=phenyl, R$^1$=CO$_2$Me, Example 3a), 12.50 g (85.60 mmol) of 2-acetylamino-acrylic acid-methylester (V) (R$^2$=Me, R$^3$=Me) and 0.18 g of hydroquinone were mixed with 10 ml of acetonitrile and heated under stirring at 50° C.-60° C. After ca. 3 days, the crystallized product was isolated, after addition of 30 ml of diisopropylether and stirring for 2 hours at 10° C. Yield of this fraction: 17.59 g (56%). The filtrate was evaporated and the same reaction and isolation procedure was repeated once to give a combined yield of 23.51 g (74.2%) of the title product.

LC-MS: MH$^+$ 389.

$^1$H NMR: 1.32 (d, 3H, H-15), 1.82 (m, 2H, H-4), 1.83 (s, 3H, H-12), 1.84, 2.26 (m, 2H, H-3), 1.74, 2.62 (m, 2H, H-6), 2.23, 2.38 (m, 2H, H-5), 3.52 (s, 3H, H-20), 3.58 (s, 3H, H-13), 4.44 (q, 1H, H-14), 4.44 (m, 1H, H-7), 7.18 (m, 1H, H-19), 7.25 (m, 2H, H-17), 7.28 (m, 2H, H-18), 8.32 (d, 1H, H-9);

$^{13}$C NMR: 21.62 (C-4), 22.29 (C-12), 24.35 (C-15), 27.90 (C-5), 32.72 (C-3), 36.72 (C-6), 49.39 (C-7), 51.67 (C-13), 51.76 (C-20), 56.68 (C-2), 60.44 (C-14), 126.06 (C-17), 126.27 (C-19), 128.03 (C-18), 145.45 (C-16), 168.97 (C-11), 172.39 (C-8), 172.66 (C-10), 176.76 (C-1).

Example 8

Ethyl (1S,2E)-1-[(2S)-2-acetamido-3-methoxy-3-oxo-propyl]-2-[(1S)-1-phenylethyl]imino-cyclopentanecarboxylate (Compound (VI) (Wherein Ar=Phenyl, R$^1$=CO$_2$Et, R$^2$=Me, R$^3$=Me) from Compound (IV) (Wherein Ar=Phenyl, R$^1$=CO$_2$Et) and Compound (V) (Wherein R$^2$=Me, R$^3$=Me) (Step A)

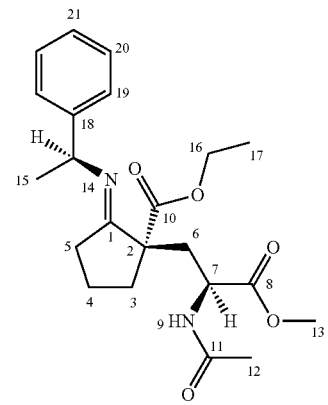

32.0 g (0.123 mol) of 2-[(S)-1-phenyl-ethylamino]-cyclopent-1-ene-carboxylic acid ethylester (IV) (Ar=phenyl, $R^1$=$CO_2Et$), prepared in a strictly analogous manner as described in Example 2 from 2-oxo-cyclopentane-carboxylic acid ethylester (purity 96%, Aldrich) and (S)-1-phenyl-ethylamine (purity>99%, BASF), and 18.0 g (0.125 mol) of 2-acetylamino-acrylic acid-methylester (V) ($R^2$=Me, $R^3$=Me) were reacted in an analogous manner as described in example 7 to give 25.0 g of the title compound as a first crystallization fraction. Further product contained in the mother liquor was not isolated.

$^1$H NMR: 1.02 (t, 3H, H-17), 1.33 (d, 3H, H-15), 1.82 (m, 2H, H-4), 1.81 (s, 3H, H-12), 1.84, 2.25 (m, 2H, H-3), 1.72, 2.62 (2dd, 2H, H-6), 2.23, 2.38 (m, 2H, H-5), 3.58 (s, 3H, H-13), 3.98 (q, 2H, H-17), 4.43 (q, 1H, H-14), 4.43 (m, 1H, H-7), 7.18 (m, 1H, H-21), 7.25 (m, 2H, H-19), 7.28 (m, 2H, H-20).

X-Ray Crystallographic Analysis:

A specimen of the title compound was used for the X-ray crystallographic analysis. The X-ray intensity data were measured. The total exposure time was 12.01 hours. The frames were integrated with the Bruker SAINT software package using a narrow-frame algorithm. The integration of the data using an orthorhombic unit cell yielded a total of 8017 reflections to a maximum 8 angle of 49.94° (1.01 Å resolution), of which 2249 were independent (average redundancy 3.565, completeness=98.7%, $R_{int}$=2.37%, $R_{sig}$=2.32%) and 2026 (90.08%) were greater than $2\sigma(F^2)$. The final cell constants of a=9.2601(4) Å, b=13.3630(6) Å, c=18.2369(8) Å, volume=2256.68(17) Å$^3$, are based upon the refinement of the XYZ-centroids of 2561 reflections above 20 σ(I) with 8.202°<2θ<91.28°. Data were corrected for absorption effects using the multi-scan method (SADABS). The ratio of minimum to maximum apparent transmission was 0.910. The structure was solved and refined using the Bruker SHELXTL Software Package, using the space group P 21 21 21, with Z=4 for the formula unit, $C_{22}H_{30}N_2O_5$. The resulting absolute configuration was as drawn above and in Scheme 3.

Example 9

Methyl (1S,2E)-1-[(2S)-3-methoxy-3-oxo-2-[(2,2,2-trifluoroacetyl)amino]propyl]-2-[(1S)-1-phenylethyl]imino-cyclopentanecarboxylate (Compound (VI) (Wherein Ar=Phenyl, $R^1$=$CO_2Me$, $R^2$=Me, $R^3$=$CF_3$) from Compound (IV) (Wherein Ar=Phenyl, $R^1$=$CO_2Me$) and Compound (V) (Wherein $R^2$=Me, $R^3$=$CF_3$) (Step A)

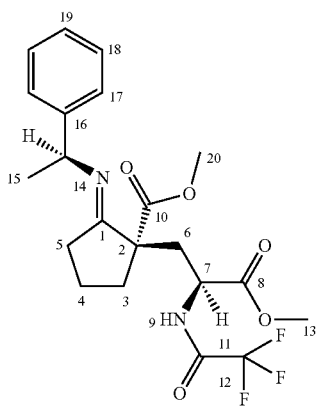

4.13 g (16.84 mmol) of 2-[(S)-1-phenyl-ethylamino]-cyclopent-1-ene-carboxylic acid-methylester (IV), (Ar=phenyl, $R^1$=$CO_2Me$, Example 3a), 0.06 g of hydroquinone, 3.32 g (16.84 mmol) of 2-trifluoroacetylamino-acrylic acid-methylester (V) ($R^2$=Me, $R^3$=$CF_3$, Darses et al. JAGS, 2008, vol. 130, no. 19, p. 6159-6169) and 1.5 ml of acetonitrile were heated at 60° C. under argon atmosphere. Conversion within seven hours was 75% according to LC-MS analysis and the mixture was evaporated i.vac. to afford 7.59 g of a crude product containing the title compound and some unreacted starting material. LC-MS: MH$^+$ 443.

$^1$H NMR: 1.32 (d, 3H, H-15), 1.82 (m, 2H, H-4), 1.84, 2.26 (m, 2H, H-3), 2.00, 2.73 (m, 2H, H-6), 2.23, 2.38 (m, 2H, H-5), 3.56 (s, 3H, H-20), 3.67 (s, 3H, H-13), 4.45 (q, 1H, H-14), 4.69 (m, 1H, H-7), 7.18 (m, 1H, H-19), 7.25 (m, 2H, H-17), 7.28 (m, 2H, H-18), 9.90 (d, 1H, H-9);

Example 10

Dimethyl (2S)-1-formyl-6a-[[(1S)-1-phenylethyl]amino]-3,4,5,6-tetrahydro-2H-cyclopenta[b]pyrrole-2,3a-dicarboxylate (Compound (VI') Wherein Ar=Phenyl, $R^1$=$CO_2Me$, $R^2$=Me, Scheme 4), Respectively, from Compound (IV) (Wherein Ar=Phenyl, $R^1$=$CO_2Me$) and Compound (V) (Wherein $R^2$=Me, $R^3$=H) (Step A)

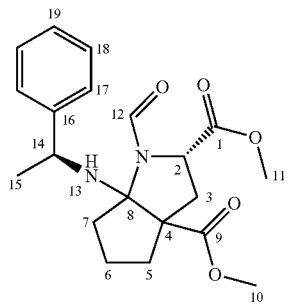 [SMILES: COC(=O)[C@@H]1CC2(C(=O)OC)CCCC2(N[C@@H](C)c2ccccc2)N1C=O]

The synthesis was performed in an analogous manner as described in example 7. The following NMR data refer to the major stereoisomer of the bicyclic reaction product (content according to NMR data ca. 90%) in the crude product mixture.

$^1$H NMR: 1.21 (d, 3H, H-15), 1.54, 2.16 (m, 2H, H-5), 1.39, 1.58 (m, 2H, H-6), 1.61, 1.94 (m, 2H, H-7), 2.19 (m, 1H, H-13), 2.33, 2.52 (m, 2H, H-3), 3.70 (s, 3H, H-11), 3.71 (s, 3H, H-10), 3.96 (q, 1H, H-14), 4.46 (dd, 1H, H-2), 7.18 (m, 1H, H-19), 7.28 (m, 2H, H-18), 7.33 (m, 2H, H-17), 8.47 (s, 1H, H-12);

$^{13}$C NMR: 21.46 (C-6), 26.36 (C-15), 32.82 (C-5), 33.27 (C-3), 34.02 (C-7), 52.06 (C-10, C-14), 52.22 (C-11), 55.90 (C-2), 63.45 (C-4), 91.03 (C-8), 126.31 (C-17), 126.36 (C-19), 128.02 (C-18), 147.63 (C-16), 160.35 (C-12), 172.42 (C-9), 172.51 (C-1).

NMR spectra show the content of non-cyclized structure of formula (VI), wherein Ar=phenyl, $R^1$=$CO_2Me$, R2=Me) to be below 3%. Equilibrium is in favor of compound VI' as shown in scheme 4).

Example 11

Methyl (1S,2E)-1-[(2S)-2-acetamido-3-methoxy-3-oxo-propyl]-2-[(1S)-1-(4-methoxyphenyl)ethyl]imino-cyclopentanecarboxylate (Compound (VI)) (Wherein Ar=4-Methoxyphenyl, $R^1$=$CO_2Me$, $R^2$=Me, $R^3$=Me) from Compound (IV) (Wherein Ar=4-Methoxyphenyl, $R^4$=$CO_2Me$) and Compound (V) (Wherein $R^2$=Me, $R^3$=Me)) (Step A))

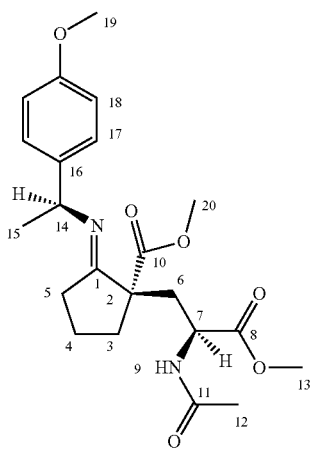 [SMILES: COC(=O)[C@H](C[C@@]1(C(=O)OC)CCC/C1=N\[C@H](C)c1ccc(OC)cc1)NC(C)=O]

The title compound was prepared in an analogous manner as described in example 7 from 3.00 g (10.9 mmol) of compound (IV) (Ar=4-methoxyphenyl, $R^1$=$CO_2Me$, Example 2) and 1.64 g (11.4 mmol) of compound (V) ($R^2$=Me, $R^3$=Me) using 10 ml of MTBE as a solvent. 3.00 g (66%) of the title product were obtained as viscous orange oil after washing the crude product three times with diisopropylether.
LC-MS: $MH^+$ 419
$^1$H NMR: 1.30 (d, 3H, H-15), 1.82 (m, 2H, H-4), 1.83 (s, 3H, H-12), 1.84, 2.25 (m, 2H, H-3), 1.74, 2.62 (m, 2H, H-6), 2.23, 2.38 (m, 2H, H-5), 3.52 (s, 3H, H-20), 3.59 (s, 3H, H-13), 3.73 (s, 3H, H-19), 4.38 (q, 1H, H-14), 4.43 (m, 1H, H-7), 6.85 (d, 2H, H-17), 7.15 (d, 2H, H-18), 8.33 (d, 1H, H-9);

Preparation of Compounds of Formulae (VII), Incl. (VIIa), (VIIb), and of (VII'), Incl. (VIIa') and (VIIb')

Example 12

Methyl (2S)-2-acetamido-3-[(1R)-1-cyano-2-oxo-cyclopentyl]-propanoate (compound (VII)) ($R^1$=CN, $R^2$=Me, $R^3$=Me) from compound (VI) (wherein Ar=phenyl, $R^1$=CN, $R^2$=Me, $R^3$=Me) (step B-1))

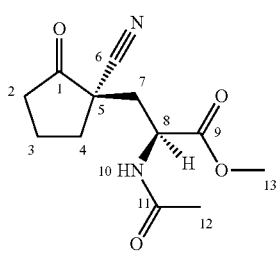 [SMILES: COC(=O)[C@H](C[C@@]1(C#N)CCCC1=O)NC(C)=O]

18.00 g (50.64 mmol) of compound (VI) (Ar=phenyl, $R^1$=CN, $R^2$=Me, $R^3$=Me, Example 5), 5.00 g (83.3 mmol) of acetic acid and 40 ml of water were heated under stirring at 50-55° C. The suspension became clear within 45 minutes and the reaction was complete after 90 minutes (LC-MS). The product partially crystallized from the reaction mixture upon cooling. The crystals were washed with small portions of cold water. The filtrate was acidified with 25 ml of 2N hydrochloric acid, and the combined aqueous phases were concentrated to ca. 30 ml and extracted 5 times with ethyl acetate. The combined extracts were evaporated and the product crystallized from a small volume of hot dichloromethane and MTBE to give a total of 12.13 g (95%) of the title compound.
LC-MS: $MH^+$ 253.
$^1$H NMR: 1.86 (s, 3H, H-12), 1.92 (m, 2H, H-3), 1.99, 2.25 (2dd, 2H, H-7), 2.00, 2.15 (2m, 2H, H-4), 2.37 (m, 2H, H-2), 3.64 (s, 3H, H-13), 4.47 (ddd, 1H, H-8), 8.45 (d, 1H, H-10).

The chiral auxiliary (S)-1-phenyl-ethylamine can be recovered from the alkalinized aqueous phase by extraction and distillation.

Preparation of Compounds of Formula (VIIa) and (VIIa')

Example 13

Methyl (1S)-1-[(2S)-2-acetamido-3-methoxy-3-oxo-propyl]-2-oxo-cyclopentane carboxylate (Compound (VII)) (Wherein $R^1$=$CO_2Me$, $R^2$=Me, $R^3$=Me) from Compound (VI) (Wherein Ar=Phenyl, $R^1$=$CO_2Me$, $R^2$=Me, $R^3$=Me)) (Step B-1)

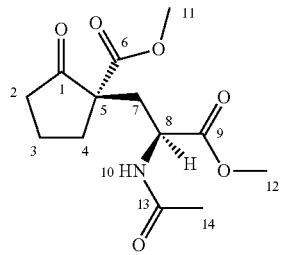 [SMILES: COC(=O)[C@H](C[C@@]1(C(=O)OC)CCCC1=O)NC(C)=O]

17.10 g (44.02 mmol) of compound (VI) (Ar=phenyl, $R^1$=$CO_2Me$, $R^2$=Me, $R^3$=Me; Example 7), 3.17 g (52.82 mmol) of acetic acid and 27 ml of water were heated under stirring at 50° C. The reaction was complete after 5 hours (LC-MS). The reaction mixture was acidified with dilute hydrochloric acid and extracted exhaustively with ethyl acetate. The combined extracts were washed with a small amount of dilute hydrochloric acid, dried over $MgSO_4$ and evaporated. The product crystallized from a mixture of MTBE/acetone (ca. 5/1, 50 ml) to give a total of 11.20 g (89%) of the title compound.
LC-MS: $MH^+$ 286.
$^1$H NMR: 1.81 (s, 3H, H-14), 1.78 (dd, 1H, J=14.3, 8.7 Hz, H-7), 2.41 (dd, 1H, J=14.3, 5.9 Hz, H-7'), 1.90, (m, 2H, H-3), 1.99, 2.43 (2m, 2H, H-4), 2.30 (m, 2H, H-2), 3.58 (s, 3H, H-12), 3.60 (s, 3H, H-11), 4.39 (ddd, 1H, J=8.7, 8.4, 5.9 Hz, H-8), 8.25 (d, 1H, J=8.4 Hz, H-10).
$^{13}$C NMR: 19.28 (C-3), 22.26 (C-14), 31.84 (C-4), 36.68 (C-2), 34.65 (C-7), 48.77 (C-8), 51.85 (C-12), 52.44 (C-11), 58.54 (C-5), 169.14 (C-13), 170.01 (C-6), 213.45 (C-1).

Example 14

Ethyl (1S)-1-[(2S)-2-acetamido-3-methoxy-3-oxo-propyl]-2-oxo-cyclopentane carboxylate (Compound (VII) (Wherein $R^1=CO_2Et$, $R^2=Me$, $R^3=Me$) from Compound (VI) (Wherein Ar=Phenyl, $R^1=CO_2Et$, $R^2=Me$, $R^3=Me$)) (Step B-1)

The compound was prepared in an analogous manner as described in Example 13 from compound (VI) (Ar=phenyl, $R^1=CO_2Et$, $R^2=Me$, $R^3=Me$) as prepared in Example 8.

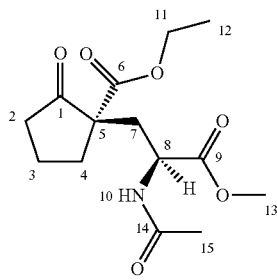 [SMILES: CCOC(=O)[C@]1(C[C@H](NC(C)=O)C(=O)OC)CCCC1=O]

$^1$H NMR: 1.16 (t, 3H, J=7.1 Hz, H-12), 1.81 (s, 3H, H-15), 1.76 (dd, 1H, J=14.4, 9.0 Hz, H-7), 2.41 (dd, 1H, J=14.4, 5.6 Hz, H-7'), 1.90, (m, 2H, H-3), 1.99, 2.42 (2m, 2H, H-4), 2.30 (m, 2H, H-2), 3.58 (s, 3H, H-13), 4.05 (q, 2H, J=7.1 Hz, H-11), 4.41 (ddd, 1H, J=9.0, 8.4, 5.6 Hz, H-8), 8.25 (d, 1H, J=8.4 Hz, H-10).

$^{13}$C NMR: 19.32 (C-3), 22.26 (C-15), 31.84 (C-4), 36.64 (C-2), 34.60 (C-7), 48.79 (C-8), 51.82 (C-13), 58.62 (C-5), 61.09 (C-11), 169.13 (C-14), 169.49 (C-6), 213.51 (C-1).

Example 15

Methyl (1S)-1-[(2S)-3-methoxy-3-oxo-2-[(2,2,2-trifluoroacetyl)-amino]propyl]-2-oxo-cyclopentanecarboxylate (Compound (VII) (Wherein $R^1=CO_2Me$, $R^2=Me$, $R^3=CF_3$) from Compound (VIa) (Wherein Ar=Phenyl, $R^1=CO_2Me$, $R^2=Me$, $R^3=CF_3$) (Step B-1)

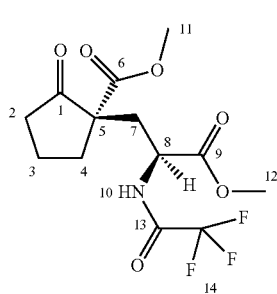 [SMILES: COC(=O)[C@H](C[C@@]1(C(=O)OC)CCCC1=O)NC(=O)C(F)(F)F]

2.00 g of crude compound (VI) (wherein Ar=phenyl, $R^1=CO_2Me$, $R^2=Me$, $R^3=CF_3$) obtained in Example 9 were dissolved in a mixture of acetic acid (0.35 ml), water (1 ml) and acetonitrile (2 ml) and were heated under stirring at 50° C. The reaction was complete after one hour (LC-MS). The reaction mixture was acidified with dilute hydrochloric acid and extracted twice with MTBE. The combined extracts were washed with a pH 5 buffer solution and brine, dried over MgSO$_4$ and evaporated to give 1.47 g of yellow oil which was composed of ca. 70% of the target compound and ca. 20% of the enaminoester (IV) (wherein Ar=phenyl, $R^1=CO_2Me$). The crude product was subjected to column chromatography on silica gel (heptane/ethylacetate) to afford 1.23 g of the pure title compound as colourless oil. LC-MS: MH$^+$ 340.

$^1$H NMR: 1.80-2.04 (m, 4H, H-3, H-4), 2.23-2.47 (m, 3H, H-2, H-7), 2.57 (dd, 1H, H7'), 3.60 (s, 3H, H-12), 3.65 (s, 3H, H-11), 4.57 (m, 1H, H-8), 9.88 (d, 1H, H-10).

Example 16

Dimethyl (2S)-1-formyl-6a-hydroxy-3,4,5,6-tetrahydro-2H-cyclopenta[b]pyrrole-2,3a-dicarboxylate (Compound (VII') Wherein $R^1=CO_2Me$, $R^2=Me$)) (Step B-1)

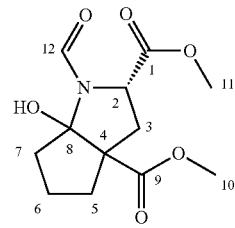

The synthesis of the title compound was performed analogously as described in Example 13 starting from compound (VI') (wherein Ar=phenyl, $R^1=CO_2Me$, $R^2=Me$) obtained in Example 10 (partly containing compound (VI) wherein Ar=phenyl, $R^1=CO_2Me$, $R^2=Me$, $R^3=H$). The following NMR data refer to the major stereoisomer (ca. 90%) of the bicyclic reaction product contained in the crude product mixture (1.80 g, yield 69%).

$^1$H NMR: 1.45, 1.75 (m, 2H, H-6), 1.63, 2.26 (m, 2H, H-5), 2.21, 2.29 (m, 2H, H7), 2.16, 2.48 (m, 2H, H-3), 3.62 (s, 3H, H-10), 3.64 (s, 3H, H-11), 4.29 (dd, 1H, H-2), 6.58 (s, 1H, 8-OH), 8.39 (s, 1H, H-12).

$^{13}$C NMR: 21.41 (C-6), 33.13 (C-5), 34.06 (C-3), 38.17 (C-7), 51.86 (C-11), 52.01 (C-10), 56.58 (C-2), 61.56 (C-4), 101.03 (C-8), 161.22 (C-12), 170.96 (C-1), 172.49 (C-9).

The crude title compound was subjected to acid hydrolysis (aqueous HCl) according to step B-3 as described in the subsequent example 17. The crude amino acid of formula (VIII)

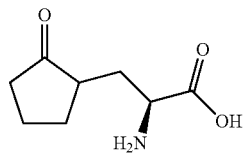

(VIII)

was obtained as a hydrochloride salt in quantitative yield and analysed by $^1$H NMR spectroscopy (DMSO-d$_6$): 1.20-2.45 (m, 9H), 3.93 (m, 1H, CHN), 8.50 (s, 3H, NH3$^+$).

Preparation of Compounds (IIIa), (IIIb), (II), (IX) and (I)

Example 17

Preparation of the hydrochloride of (2S,3aS,6aS)-cyclopenta[b]pyrrole-2-carboxylic acid (IIIa) from compound (VII) (wherein $R^1$=$CO_2Me$, $R^2$=Me, $R^3$=Me) (steps B-1b+C in one vessel)

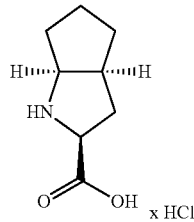
(IIIa)

20.0 g (70.1 mmol) of compound (VII) ($R^1$=$CO_2Me$, $R^2$=Me, $R^3$=Me, Example 13) were heated at ca. 100° C. with 140 ml of 1 M hydrochloric acid until LC-MS indicated the complete conversion into a product with $MH^+$ 172 (ca. 14 h). In the course of this hydrolysis process, some distillate was collected and replaced by the same volume of 1 M HCl. The reaction mixture was concentrated, diluted with 100 ml of water and concentrated again to give 23.4 g of oily product. Subsequent hydrogenation of this material was performed in the same vessel in water at pH1 at 90-100° C. using 400 mg of a 5% Pd on carbon catalyst until LC-MS indicated the complete conversion into the target product with $MH^+$ 156. The catalyst was filtered off, the filtrate was evaporated and the residue was evaporated again two times with acetone. The solid residue was stirred in acetone, filtered, washed with acetone and dried to give 10.0 g (74.4%) of the pure title compound which was proven to be identical with an authentic sample.

1H NMR ($D_2O$): 1.43-2.00 (m, 7H), 2.60 (m, 1H, H-3), 2.95 (m, 1H, H-3'), 4.15 (m, 1H, H-6a), 4.30 (m, 1H, H-2).

Example 18

Preparation of (2S,3aS,6aS)-cyclopenta[b]pyrrole-2-carboxylic acid (IIIa) from compound (VII) (wherein $R^1$=CN, $R^2$=Me, R3=Me) (step B-1b and then C)

1.00 g (3.96 mmol) of compound (VII) ($R^1$=CN, $R^2$=Me, R3=Me, Example 12) were heated at 100° C. with 5 ml of concentrated hydrochloric acid until LC-MS indicated the complete conversion into a product with $MH^+$ 172 (ca. 24 h). The solution was concentrated to ca. 3 ml and diluted with 20 ml of acetone under stirring. The supernatant was decanted and the insoluble washed again twice with acetone and dried i.vac. to yield a glassy residue (ca. 0.80 g) which was redissolved in 10 ml of water containing 0.31 g (3.75 mmol) of sodium hydrogen-carbonate. Subsequent hydrogenation was performed at 50° C. (balloon) using 10% Pd on Charcoal (50 mg) until products with $MH^+$ 172 were completely transformed into the title compound with MH+ 156, as shown by LC-MS analysis. The catalyst was removed by filtration and the filtrate was concentrated to ca. 3 ml and stirred with a mixture of acetone/isopropanol (10/1). The insoluble material was dried i. vac. to give 0.61 g (68% corr. yield) of the crude title compound as colorless solid which was contaminated with ca. 0.21 g of sodium chloride. For analytical data see the preceding example.

Example 19

Preparation of Ramipril (I) from (2S,3aS,6aS)-cyclopenta[b]pyrrole-2-carboxylic acid (IIIa) and the anhydride of the formula (X) (step D-1)

2.43 g (12.67 mmol) of the hydrochloride of (2S,3aS,6aS)-cyclopenta[b]pyrrole-2-carboxylic acid (IIIa) as prepared in Example 17 were dissolved in 10 ml of water, then a solution of 3.87 g (12.67 mmol) of the anhydride of the formula (X) was added. Aqueous 2N NaOH was added at a temperature of 10-15° C. until a pH of 9.0 was obtained, and then additional aqueous NaOH was added dropwise under stirring while keeping the pH at 8.5-9.5. The turbid mixture turned into a clear solution within ca. 30 minutes after the addition of ca. 19 ml of 2N NaOH solution. The solution as acidified to pH 5.2 using concentrated hydrochloric acid and extracted three times with ethyl acetate and brine. Evaporation of solvents provided a colourless oil which crystallized from cold diisopropylether. Yield: 3.90 g (74%) of Ramipril with >98.7% purity (LC peak area).

LC-MS: $MH^+$ 417,

1H NMR (2 rotamers) 1.06 (d, 3H, Me), 1.19 (t, 3H, Me), 1.30-2.05 (m, 8H), 2.27-2.47 (m, 1H), 2.57 (m, 2H), 2.72 (m, 1H), 3.13, 3.19 (m, 1H), 3.30 (m, 1H), 3.63 (m, 1H), 4.08 (q, 2H, OC$\underline{H}_2$CH$_3$), 4.30, 4.50 (m, 2H), 7.12-7.30 (m, 5H ArH).

Example 20

Preparation of the hydrochloride of (2S,3aS,6aS)-cyclopenta[b]pyrrole-2-carboxylic acid benzylester (IIIb) from (2S,3aS,6aS)-cyclopenta[b]pyrrole-2-carboxylic acid (IIIa) (step D-2a)

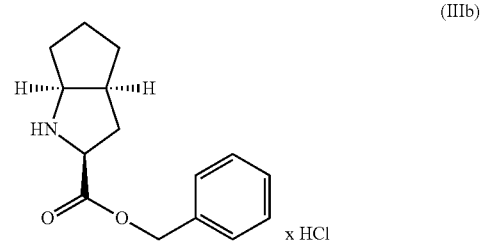 [SMILES: O=C(OCc1ccccc1)[C@@H]1C[C@@H]2CCC[C@@H]2N1]
(IIIb)

5.00 g (26.09 mmol) of the hydrochloride of (2S,3aS, 6aS)-cyclopenta[b]pyrrole-2-carboxylic acid (IIIa) as prepared in Example 17 were suspended in 30.0 ml (0.29 mol) of benzylalcohol at 0° C. and 5.0 ml (68.9 mmol) of thionylchloride were added slowly at <5° C. The mixture was slowly warmed up to room temperature. After ca. 2 days stirring, the mixture was diluted with 120 ml of MTBE. The solid was isolated by filtration, washed with MTBE and dried to obtain 7.06 g (96%) of the hydrochloride of the title compound as a grey-white powder. Peak area LC-MS>99%,

LC-MS: $MH^+$ 246.

1H NMR: 1.40-1.83 (m, 6H, H-4, H-5, H-6), 1.95 (m, 1H, H-3), 2.48 (m, 1H, H-3') 2.82 (m, 1H, H-3a), 3.98 (m, 1H,

H-6a), 4.45 (m, 1H, H-2), 5.25 (dd, 2H, OCH$_2$), 7.40 (m, 5H, Ar), 8.80-10.50 (brm, 2H, NH)

Chiral HPLC analysis: Column Chiralpak IA/124, dimensions 250×4.6 mm with eluent mixture of heptane/ethanol/methanol 20/1/1+0.1% diethylamine. The retention times were 7.60 minutes for (2R,3aR,6aR)-cyclopenta[b]pyrrole-2-carboxylic acid benzylester (peak area<0.01%) and 8.05 minutes for (2S,3aS,6aS)-cyclopenta[b]pyrrole-2-carboxylic acid benzylester (>99.9%). The enantiomeric excess was ee>99.8%. For comparison, a commercial sample of the all-S isomer purchased from Aldrich Chemicals showed a ratio all-S/all-R of 98.61/1.39% (ee 97.2%) by using the same assay.

Example 21

Preparation of Ramipril-benzylester (XI) from (2S, 3aS,6aS)-cyclopenta[b]pyrrole-2-carboxylic acid-benzylester (IIIb, R=Bn) and the anhydride of the formula (X) (step D-2b-1)

1.90 g (6.74 mmol) of the hydrochloride of (2S,3aS,6aS)-cyclopenta[b]pyrrole-2-carboxylic acid-benzylester (111b, R=Bn, Example 20) were added to a stirred mixture of 0.83 g (9.83 mol) of sodium hydrogencarbonate in 5 ml of water and 20 ml of ethyl acetate at 15° C. After 5 minutes, a solution of 2.00 g (6.55 mmol) of the anhydride of the formula X in 5 ml of ethyl acetate was added dropwise within 5 minutes. Stirring was continued at ambient temperature for 60 minutes, the organic phase was separated, washed twice with saturated aqueous sodium hydrogen carbonate, dried and evaporated to dryness i.vac. (ca. 30° C./up to 1 mbar) to give 3.30 g (99%) of the title compound as colorless oil. LC-MS purity was >98% (peak area) (MH$^+$ 507). The $^1$H NMR data of this product were undistinguishable from the data obtained with the product being prepared in Example 22.

Example 22

Conversion of N-[1-(S)-(ethoxycarbonyl)-3-phenyl-propyl]-L-alanine (II) into Ramipril-benzylester (XI) using the Vilsmeier reagent (XII) (step D-2b-2)

0.70 ml (9.62 mmol) thionylchloride were added dropwise under argon and cooling to 0.67 g (9.17 mmol) dry N,N-dimethylformamide. The mixture was stirred for one hour at 40° C. and then another two hours at 40° C. i.vac. (up to 1 mbar). A viscous semi-crystalline mass (1.17 g, 100%) formed upon cooling in an ice-bath. At a temperature of −10° C., this material was combined under an argon atmosphere with a suspension of 2.39 g (8.56 mmol) of N-[1-(S)-(ethoxycarbonyl)-3-phenylpropyl]-L-alanine (II) in 25 ml of dry DCM containing 10 mmol of dry HCl. The mixture became a clear solution within ca. 10 minutes and was stirred further 15 minutes in a temperature range from −10° C. to −5° C. The cold solution was then transferred within ca. 3 minutes into a vigorously stirred mixture of water (5 ml), sodium bicarbonate (3.4 g), DCM (5 ml) and 2.00 g (8.15 mmol) of (2S,3aS,6aS)-cyclopenta[b]pyrrole-2-carboxylic acid-benzylester (IIIb, R=Bn, Example 20). The organic phase was separated, washed 3 times with 5 ml of water, dried over sodium sulfate and carefully concentrated at 25° C./1 mbar to yield 4.11 g (99.5%) of crude Ramipril-benzylester (XI) as a clear oil. LC-MS purity was 96.6% (peak area) (MH$^+$ 507).

$^1$H NMR (2 conformers) 1.03 (d, 3H, Me), 1.18 (t, 3H, Me), 1.25-2.45 (m, 10H), 2.57 (m, 2H), 2.73 (m, 1H), 3.13 (m, 1H), 3.62 (m. 1H), 4.08 (q, 2H, OC$\underline{H}_2$CH$_3$), 4.33 (m, 1H), 4.47, 4.73 (m, 1H), 5.10 (q, 2H, OBn), 7.10-7.40 (m, 10H Ar—H).

Example 23

Preparation of Ramipril (I) from Ramipril-Benzylester (XI) (Step D-2c)

4.1 g (8.09 mmol) of Ramipril-benzylester (XI) obtained in Example 21 were hydrogenated at 15-20° C. in 30 ml of methanol with a 10% Pd on charcoal catalyst (ca. 100 mg) at atmospheric pressure (balloon). After complete consumption of the starting material, as detected by LC-MS, the catalyst was filtered off and the solvent was evaporated i.vac. In this manner, crude Ramipril was obtained as viscous oil in almost quantitative yield (3.35 g).

A sample was crystallized from acetone and exhibited >99.9 purity (LC-MS peak area at 220 nm). Analytical data—same as in Example 19.

The invention claimed is:

1. A process for preparing a compound of formula (VI)

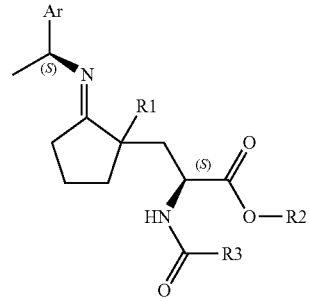

(VI)

wherein:
R1 is CO$_2$R4 or CN;
R2 is (C1-C4)alkyl;
R3 is
  (C1-C4)alkyl, wherein one, two or three hydrogen atoms are optionally replaced by fluorine, (C1-C4) alkoxy, or
  phenyl;
R4 is (C1-C4)alkyl; and
Ar is
  phenyl, optionally substituted with one, two or three substituents independently selected from the group consisting of halogen, (C1-C4)alkoxy and (C1-C4) alkyl, or
  1-naphthyl;
comprising
reacting a chiral amine of formula (IV)

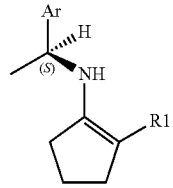

(IV)

wherein:
R1 is CO$_2$R4 or CN;
R4 is (C1-C4)alkyl; and

Ar is
  phenyl, optionally substituted with one, two or three substituents independently selected from the group consisting of halogen, (C1-C4)alkoxy and (C1-C4) alkyl, or
  1-naphthyl;
with a 2-acylamino-acrylic acid ester of formula (V)

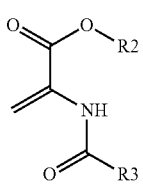

wherein:
R2 is (C1-C4)alkyl; and
R3 is
  (C1-C4)alkyl, wherein one, two or three hydrogen atoms are optionally replaced by fluorine, (C1-C4) alkoxy, or
  phenyl,
to produce the compound of formula (VI).

2. A compound of formula (VI)

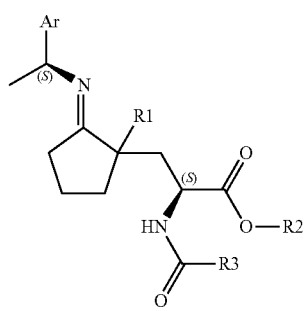

wherein:
R1 is $CO_2R4$ or CN;
R2 is (C1-C4)alkyl;
R3 is
  (C1-C4)alkyl, wherein one, two or three hydrogen atoms are optionally replaced by fluorine, (C1-C4) alkoxy, or
  phenyl;
R4 is (C1-C4)alkyl; and
Ar is
  phenyl, optionally substituted with one, two or three substituents independently selected from the group consisting of halogen, (C1-C4)alkoxy and (C1-C4) alkyl, or
  1-naphthyl.

3. The compound according to claim 2, wherein the carbon atom bearing the R1 group is in the (S) configuration.

4. A compound of formula (VIIa)

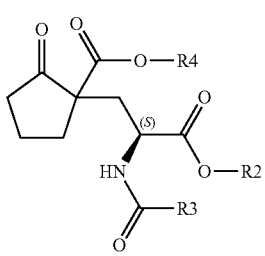

wherein:
R2 is (C1-C4)alkyl;
R3 is
  (C1-C4)alkyl, wherein one, two or three hydrogen atoms are optionally replaced by fluorine, (C1-C4) alkoxy, or
  phenyl; and
R4 is (C1-C4)alkyl.

5. The compound of claim 4, wherein the carbon atom bearing the $CO_2R4$ group is in the (S) configuration.

6. A compound of formula (VIIb)

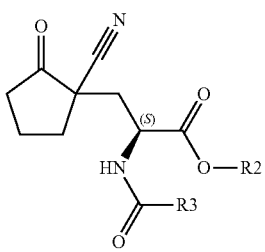

wherein:
R2 is (C1-C4)alkyl; and
R3 is
  (C1-C4)alkyl, wherein one, two or three hydrogen atoms are optionally replaced by fluorine, (C1-C4) alkoxy, or
  phenyl.

7. The compound of claim 6, wherein the carbon atom bearing the CN group is in the (R) configuration.

8. The compound according to claim 2, wherein R1 is $CO_2R4$.

9. The compound according to claim 2, wherein R2 is methyl or ethyl.

10. The compound according to claim 2, wherein R3 is methyl, ethyl, propyl, butyl, trifluoromethyl, methoxy, ethoxy, propoxy, butoxy, or phenyl.

11. The compound according to claim 2, wherein R4 is methyl or ethyl.

12. The compound according to claim 2, wherein Ar is phenyl, 4-methoxyphenyl, 4-chlorophenyl or 1-naphthyl.

13. The compound according to claim 4, wherein R2 is methyl or ethyl.

14. The compound according to claim 4, wherein R3 is methyl, ethyl, propyl, butyl, trifluoromethyl, methoxy, ethoxy, propoxy, butoxy, or phenyl.

15. The compound according to claim 4, wherein R4 is methyl or ethyl.

16. The process of claim 1, further comprising steps (B-1a), (B-1b), (C), and (D):

(B-1a) hydrolysing the chiral imine moiety in the compound of formula (VI) to produce a chiral ketone of formula (VII),

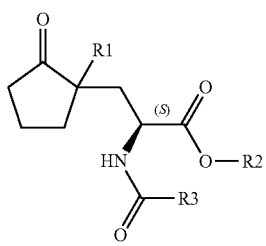
(VII)

wherein:

R1 is CO₂R4 or CN;

R2 is (C1-C4)alkyl;

R3 is
(C1-C4)alkyl, wherein one, two or three hydrogen atoms are optionally replaced by fluorine, (C1-C4) alkoxy, or
phenyl; and R4 is (C1-C4)alkyl;

followed by (B-1b) hydrolysing the chiral ketone of formula (VII) to produce a chiral amino acid of formula (VIII), or a salt thereof,

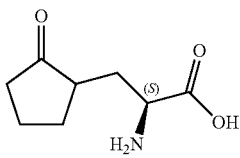
(VIII)

which is in equilibrium with a chiral bicyclic amino acid of formula (IX), or a salt thereof,

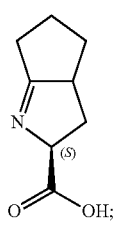
(IX)

and (C) converting the chiral bicyclic amino acid of formula (IX) or salt thereof, from the mixture of the chiral amino acid of formula (VIII) or salt thereof, and the chiral bicyclic amino acid of formula (IX) or salt thereof, by catalytic hydrogenation into a compound of formula (IIIa), or a salt thereof,

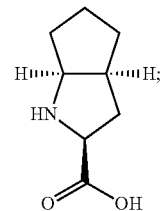
(IIIa)

and (D) converting the compound of formula (IIIa) or salt thereof into a compound of formula (I)

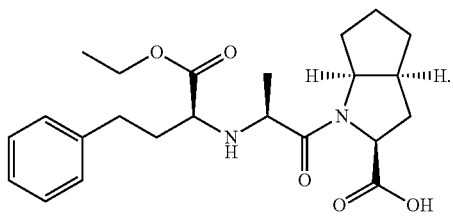
(I)

17. The process of claim 1, further comprising steps (B-2), (C), and (D):

(B-2) hydrolysing the chiral imine in the compound of formula (VI) to produce a chiral amino acid of formula (VIII), or a salt thereof,

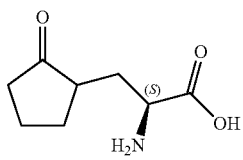
(VIII)

which is in equilibrium with a chiral bicyclic amino acid of formula (IX), or a salt thereof,

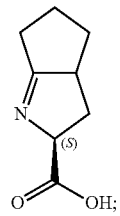
(IX)

and (C) converting the chiral bicyclic amino acid of formula (IX) or salt thereof, from the mixture of the chiral amino acid of formula (VIII) or salt thereof, and the chiral bicyclic amino acid of formula (IX) or salt thereof, by catalytic hydrogenation into a compound of formula (IIIa), or a salt thereof,

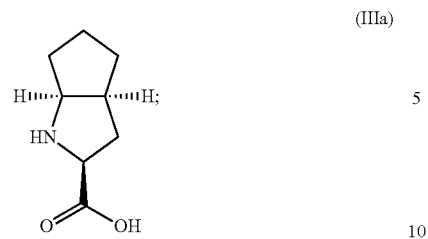
(IIIa)
and
(D) converting the compound of formula (IIIa) or salt thereof into a compound of formula (I)
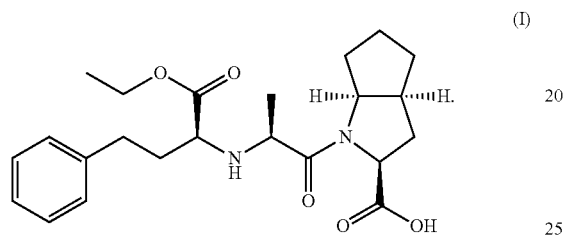
(I)
* * * * *